US 7,811,807 B2

(12) United States Patent
Kvederas et al.

(10) Patent No.: US 7,811,807 B2
(45) Date of Patent: Oct. 12, 2010

(54) NUCLEIC ACID PURIFICATION

(75) Inventors: Rimantas Kvederas, Vilnius (LT); Asta Siksniute, Vilnius (LT); Alyimantas Markauskas, Vilnius (LT)

(73) Assignee: Fermentas UAB, Vilnius (LT)

( * ) Notice: Subject to any disclaimer, the term of this patent is extended or adjusted under 35 U.S.C. 154(b) by 0 days.

(21) Appl. No.: 10/106,824

(22) Filed: Mar. 27, 2002

(65) Prior Publication Data
US 2003/0109696 A1 Jun. 12, 2003

(30) Foreign Application Priority Data
Mar. 27, 2001 (GB) .................................. 0107634.8

(51) Int. Cl.
*C12N 1/08* (2006.01)
*C12Q 1/68* (2006.01)
*G01N 33/00* (2006.01)
*C07H 21/04* (2006.01)

(52) U.S. Cl. ........................... 435/270; 435/6; 436/94; 536/23.1

(58) Field of Classification Search ............ 536/22.1, 536/23.1, 25.1, 25.3, 25.6; 435/6, 803; 210/637
See application file for complete search history.

(56) References Cited

U.S. PATENT DOCUMENTS

| | | | | |
|---|---|---|---|---|
| 4,623,723 | A | | 11/1986 | Keller et al. |
| 4,861,718 | A | * | 8/1989 | Hirata et al. ............. 435/207 |
| 5,256,294 | A | * | 10/1993 | van Reis ................. 210/637 |
| 6,011,148 | A | * | 1/2000 | Bussey et al. ........... 536/25.4 |
| 6,313,285 | B1 | * | 11/2001 | Butler et al. ............. 536/25.4 |
| 6,350,382 | B1 | * | 2/2002 | Schick .................... 210/637 |
| 2002/0198372 | A1 | * | 12/2002 | Bridenbaugh et al. ... 536/25.4 |
| 2004/0076980 | A1 | | 4/2004 | Charlton et al. |

FOREIGN PATENT DOCUMENTS

| | | |
|---|---|---|
| AU | 723817 | 8/1998 |
| EP | 0442026 | 8/1991 |
| EP | 0 517 515 A2 * | 12/1992 |
| EP | 0517515 | 12/1992 |
| EP | 0 964 057 | 12/1999 |
| WO | WO 96/36706 | 11/1996 |
| WO | WO 96/36706 A1 * | 11/1996 |
| WO | WO 98/54195 | 12/1998 |
| WO | WO 99/16869 | 4/1999 |
| WO | WO 99/16869 A1 * | 4/1999 |
| WO | WO 99/29832 | 6/1999 |
| WO | WO 00/05358 | 2/2000 |
| WO | WO 00/73318 A1 * | 12/2000 |
| WO | WO 01/07599 A1 * | 2/2001 |

OTHER PUBLICATIONS

John Blahitka, "Achieve Peak Performance in Ultrafiltration," p. I-5, (Jun. 6, 1995).*
John Blahitka, "Achieve Peak Performance in Ultrafiltration," p. 1-5, (Jun. 6, 1995).
BIO-RAD, EG Bulletin 1735, "Rapid Purification of DNA Templates with the GS Gene Prep Manifold System", 4 pages.
Birnboim et al., "A rapid alkaline extraction procedure for screening recombinant plasmic DNA," Nucleic Acids Research, Information Retrieval Limited (London England), vol. 7 (No. 6), p. 1513-1523, (Jul. 6, 1979).
"Nova Series, Omega Series, Alpha Series" Membrane Cassettes, Instruction Manual, Filtron Technology Corporation, Clinton, MA, 6 pages.
"Tangential Ultrafiltration and Microfiltration membrane Cassette Systems for Processing Volumes of 1-20 Liter Batches," Filtron Technology Corporation, Northborough, MA, 6 pages.
M. Mukhopadhyay et al., "A Simple Procedure for Large-Scale Preparation of Pure Plasmid DNA Free from Chromosomal DNA from Bacteria," Nov. 2, 1982, pp. 1-6.
Itoh et al., "Simple and rapid preparation of plasmid template by a filtration method using microliter filter plates," Nucleic Acids Res., Mar. 1997, 25(6):1315-6.

* cited by examiner

*Primary Examiner*—Bradley L Sisson
(74) *Attorney, Agent, or Firm*—Crowell & Moring LLP

(57) ABSTRACT

A process for purifying plasmid DNA from a nucleic acid containing sample comprising plasmid DNA and contaminants, which process comprises a step of contaminant removal, comprising:
(a) treating the sample to form a nucleic acid solution having a concentration of monovalent cations;
(b) contacting the nucleic acid solution with an ultrafiltration membrane having a molecular weight exclusion limit of at least 30 kDa under conditions in which substantially no gel-layer forms and in which the concentration of monovalent cations is sufficiently high for a time sufficient to remove substantially all RNA and form a retentate containing plasmid DNA; and
(c) collecting the retentate.

18 Claims, 21 Drawing Sheets

FIG. 9A
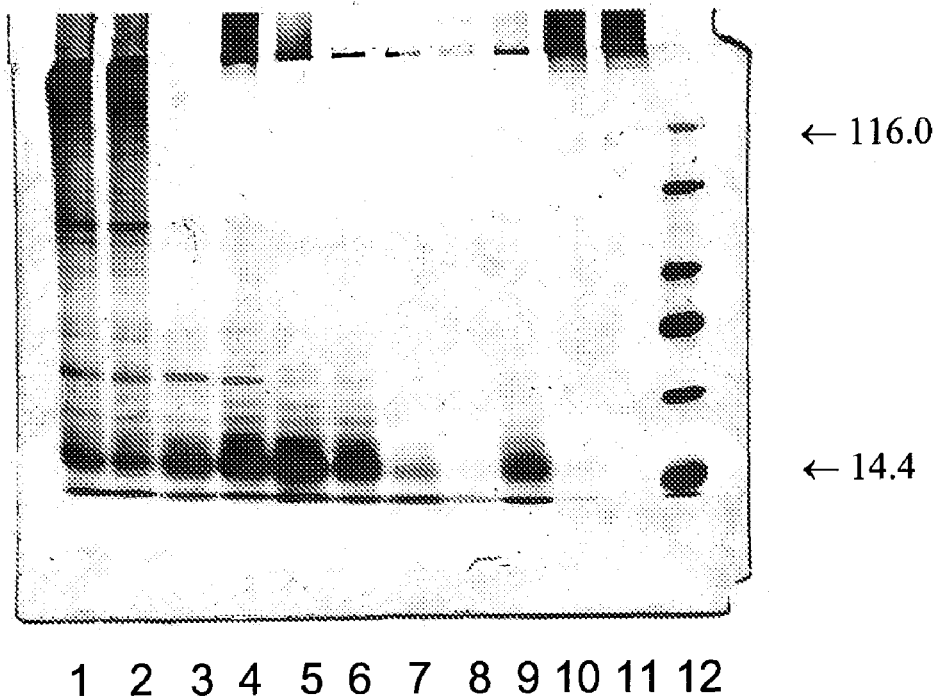
← 116.0
← 14.4
1 2 3 4 5 6 7 8 9 10 11 12
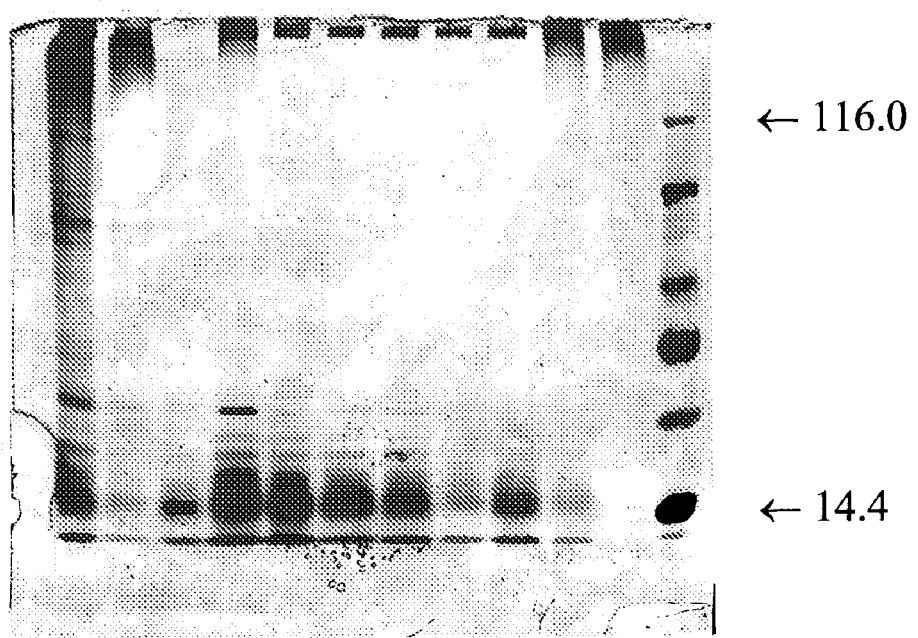
← 116.0
← 14.4
1 2 3 4 5 6 7 8 9 10 11 12
FIG. 9B

NUCLEIC ACID PURIFICATION

FIELD OF THE INVENTION

The present invention relates to a process for purifying plasmid DNA, more particularly to a process for purifying pharmaceutical grade plasmid DNA.

BACKGROUND TO THE INVENTION

The use of genetic information in the treatment of disease is one the most promising avenues of medical research. There are different approaches of delivering genetic information to a patient; most prominently among them viral vectors of different origins and "naked" DNA vectors propagated in bacteria. The use of viral vectors has been discredited of late because of safety considerations.

The use of bacterially derived plasmids in the clinic increases the importance of effective and economical means and methods of manufacturing and purifying large amounts of plasmid DNA to very high standards of purity. In order to satisfy the criteria of pharmaceutical manufacturing adopted by most authorities, a method for the purification also needs to yield reproducible and validated results.

A number of methods have been reported for the purification of pharmaceutical grade plasmid DNA. Most of them follow a similar scheme, involving a first lysis step, in which the bacteria are broken down, a subsequent denaturation step that destroys nucleic-acid interactions with proteins, and finally a procedure by which the target nucleic acid content is derived in a sequence of precipitation steps and at least one chromatographic step.

The quality obtained by these purification methods is variable. One feature, however, is that certain substances present in the bacterial biomass, among them polysaccharides derived from the bacterial cell wall, lipopolysaccharides and RNA, are difficult to remove without several chromatographic steps, and tend to contaminate the standard DNA preparations. Some of these bacterially derived contaminants are extremely potent effectors of various defence systems of higher eukaryotes, possibly because of their intrinsic function as a signal of bacterial infection. The elimination of these contaminants is a major problem in the manufacture and purification of plasmid DNA.

Ultrafiltration of biological products is known. A method for obtaining a protein from tissue fluid by diafiltration is shown in WO 98/54195. Many methods for the isolation and purification of nucleic acids are also known and taught in different patents and patent applications. For example, WO98/05673 describes a process for producing highly purified DNA which involves a combination of diafiltration and chromatography steps. Diafiltration is used before and after ion exchange chromatography primarily to ensure that the nucleic acid containing sample is in the correct buffer. A key feature of this proposal is that the diafiltration uses an open-channel or hollow fibre ultrafiltration unit to prevent turbulence at the ultrafiltration membrane so as to obtain a gel layer.

AU 723817 (derived from WO98/30685) also concerns a method for producing a highly purified plasmid DNA. In this method, two column chromatography steps are used; a Q-sepharose® chromatography step followed by a hydroxylapatite chromatography step. The eluate from the hydroxylapatite chromatography step is subjected to cross-flow filtration which is stated in the disclosure to be essential. This step is used to remove salt and other contaminants from the column eluate.

WO 00/05358 is primarily directed to the use of a static mixer to obtain a lysed cell solution in a method for purifying plasmid DNA. This, too, relies upon an ion exchange chromatography step to purify plasmid DNA and diafiltration by tangential flow using an open channel ultrafiltration unit is employed to ensure that the plasmid DNA is in the correct buffer.

U.S. Pat. No. 4,623,723 is directed to the separation of crude nucleic acid solutions using hollow fibre ultrafiltration membranes. It is proposed to separate RNA from DNA using diafiltration against deionised water. No data are given as to the effectiveness of the method.

In order to achieve highly purified pharmaceutical grade plasmid DNA, each of the above methods is primarily reliant upon a chromatographic step to remove contaminants. This can increase the time for purification, especially where multiple chromatographic steps are required, and will increase the cost involved as well.

SUMMARY OF THE INVENTION

The present invention aims to overcome the drawbacks in the prior art.

The present invention provides a process for purifying plasmid DNA from a nucleic acid containing sample comprising plasmid DNA and contaminants, which process comprises a step of contaminant removal, comprising:

(a) treating the sample to form a nucleic acid solution having a concentration of monovalent cations;

(b) contacting the nucleic acid solution with an ultrafiltration membrane having a molecular weight exclusion limit of at least 30 kDa under conditions in which substantially no gel-layer forms and in which the concentration of monovalent cations is sufficiently high for a time sufficient to remove substantially all RNA and form a retentate containing plasmid DNA; and (c) collecting the retentate.

It has surprisingly been found that a combination of particular type of ultrafiltration membrane unit and sufficient exposure to monovalent cations can remove contaminants from a plasmid DNA containing solution provided that no gel layer forms on or adjacent to the ultrafiltration membrane. In this way it is found that contaminant removal, especially RNA contaminant removal is particularly effective. This avoids the need for multiple column chromatography steps thereby keeping to a minimum the extent to which chromatography is used to purify the plasmid DNA. In the present invention a single chromatography step is sufficient to achieve the required purity of DNA. Other contaminants removed by the step of contacting the nucleic acid solution with the ultrafiltration membrane may include endotoxins and cellular proteins. This enables a relatively speedy and efficient plasmid DNA preparation capable of producing a product which is suitable for pharmaceutical application.

The monovalent cation concentration used in the present process and the time over which the nucleic acid solution is contacted with the ultrafiltration membrane in the presence of the monovalent cations may be determined empirically. Standard methods are available to determine the amount of RNA or other contaminant remaining in a test sample applied to the ultrafiltration membrane. Typically, the monovalent cation concentration is at least about 0.35M although lower concentrations may be used with a loss of some effectiveness. Generally, the monovalent cation concentration does not exceed about 2M. The monovalent cations are typically alkali metals and preferably comprise sodium or potassium. Chloride is a suitable counterion to the cations. However, lithium chloride is not found to be effective in the invention and so lithium is not a preferred monovalent cation.

Typically, the molecular weight exclusion limit of the ultrafiltration membrane does not exceed 100 kDa and is preferably at least about 50 kDa. It is not currently completely understood why the combination of elevated monovalent cation concentration and selection of molecular weight cut-off of membrane enables such effective purification of DNA from contaminants such as RNA. In the case of separating DNA from RNA, without wishing to be bound by theory, one may speculate that the molecular shape or physicochemical characteristics of RNA are altered under the process conditions such that it is able to permeate the ultrafiltration membrane whereas the plasmid DNA, especially of a size 2 Kb or larger, is unable to permeate the membrane under these conditions.

Step (b) may be conveniently used to reduce the volume of the nucleic acid solution and a volume reduction in the range of 4 to 10 fold or more is readily achievable. Advantageously, at least step (b) comprises a step of diafiltration. Conveniently, the concentration of monovalent cations may be introduced into in the nucleic acid solution by diafiltration as well. The conditions of diafiltration must be such, however, that substantially no gel-layer formation occurs. Gel-layer formation in this context is generally considered to be formation of a thin gelatinous layer of biomolecules on or in the ultrafiltration membrane. An important aspect of the present invention is a realisation that such a gel-layer may block the pores of the ultrafiltration membrane thereby reducing the efficiency and speed of filtration and causing an increase in the concentration of impurities remaining in the retentate. In practice, a good way of avoiding such gel-layer formation is to ensure that there is a degree of turbulence in the region of the ultrafiltration membrane. This may be achieved by using the ultrafiltration membrane in a screen channel ultrafiltration unit. Flow channel ultrafiltration units are typically configured so that the sample flow is in a direction normal to the direction of flow through the membrane. A screen channel ultrafiltration unit includes a separator positioned between a pair of membranes so that turbulence is generated in the retentate, in contrast to more open structures such as open channel or hollow fibre ultrafiltration units, which are not suitable for the present invention because of gel-layer formation.

Whilst the step (b) of contacting the nucleic acid with the ultrafiltration membrane may be performed at room or ambient temperature, it is preferred that an elevated temperature is used because this allows a speeding up of the filtration process. A temperature in the range 30° C. to 60° C. is preferred, most preferably around 50° C. It is also thought that elevated ultrafiltration temperatures help to decrease or prevent the formation of a gel-layer on the surface of the membrane.

Ultrafiltration may be performed at higher temperatures than 60° C., provided that the performance of the ultrafiltration membrane is not adversely affected at such high temperature. 60° C. is the highest temperature generally recommended by ultrafiltration manufacturers. The temperature must not be so high that plasmid DNA melting or denaturation begins. At temperatures as high as 60° C., ultrafiltration of plasmid DNA is found not to influence its quality, nor its subsequent use in molecular biological or gene transfer procedures. Elevated temperature is also found to be beneficial in the removal of lipopolysaccharide contamination. It is thought that a combination of high temperature, monovalent cations and other components such as calcium ions and detergent may disrupt lipopolysaccharides in aqueous solutions.

The step of contacting with the ultrafiltration membrane may be carried out once or a number of times in order to achieve the contaminant removal. Usually, a pressure gradient in the range 15 to 30 psi is adequate for the process, preferably around 20 psi.

A number of other steps may be incorporated into the process for purifying plasmid DNA in accordance with the present invention in addition to the step of contaminant removal. For example, the retentate may be subjected to a step (d) of further purification. This may conveniently be achieved by a step of chromatography typically to purify the plasmid DNA further from minor or trace contaminants. Only one such step is normally necessary although further steps can improve product DNA purity. Ion exchange chromatography is preferred, most preferably anion exchange chromatography. It is also possible use hydrophobic chromatography. A typical procedure comprises:

(i) contacting the retentate an anion exchange resin under conditions to bind plasmid DNA;

(ii) optionally washing the resin to remove impurities from the plasmid DNA; and (iii) eluting the plasmid DNA.

In a preferred arrangement a step of hydrophobic chromatography is also employed, especially before the step of ion exchange chromatography, so as to remove endotoxin and cellular protein contamination from the plasmid DNA-containing retentate.

The nucleic acid containing sample used in the process of the present invention may be prepared from a crude nucleic acid solution containing plasmid DNA and RNA. This crude nucleic acid solution is preferably treated to provide a calcium ion concentration sufficient to precipitate a majority of the large molecular weight RNA; and a solution phase is separated therefrom (M. Mukhopadhyay and N. C. Mandal—Anal.Biochem. 1983, 133, 265-270). The solution phase comprises the nucleic acid containing sample used in the step of contaminant removal. A useful calcium ion concentration is in the range 0.1M to 0.3M, preferably around 0.2M. In this way, host RNA can be substantially eliminated from the crude nucleic acid solution so as to leave of the order of 40-60% RNA in the total nucleic acid amount. Whilst this is a significant amount for pharmaceutical grade plasmid DNA preparation, in combination with the step of fine RNA removal a plasmid which is substantially RNA-free may be obtained. In practical terms, purified plasmid DNA which is RNA-free can otherwise be obtained commercially using RNase. However, for use as a therapeutic, it is essential that RNase is eliminated from the plasmid DNA purification process because RNase is an animal-derived enzyme whose use in the purification procedure introduces a possibility of contamination with infectious agents. It is also thought that the presence of calcium ions in the nucleic acid containing sample subjected to contaminant removal may assist the elimination of lipopolysaccharide and host cell protein contamination.

The crude nucleic acid solution used in the step of calcium ion precipitation is typically prepared by providing a cell free extract comprising plasmid DNA and RNA; and concentrating the extract, for example, by ultrafiltration. The extract may be concentrated by passage through an ultrafiltration membrane unit having a suitable molecular weight exclusion limit, typically of at least 30 kDa, to form the crude nucleic acid solution as a retentate. The molecular weight exclusion limit of this ultrafiltration membrane is preferably no greater than about 100 kDa and more preferably at least 50 kDa. Advantageously, passage through the ultrafiltration membrane unit is performed at a temperature in the range 30° C. to 60° C., preferably around 40° C. Such elevated temperature has the advantages discussed above in relation to the step of contaminant removal. The extract may be passed through the ultrafiltration membrane unit once or a number of times to achieve the desired concentration. This may be carried out at a pressure gradient in the range 15 psi to 30 psi, preferably around 20 psi. A reduction in volume in the range 3 to 15 fold is achievable. It is advantageous in this step to include the step of diafiltration against any suitable solution for use in the subsequent step of calcium precipitation of the RNA.

In a preferred embodiment, this step of ultrafiltration is carried out in the presence of a detergent, preferably an ionic detergent, more preferably in the presence of an anionic detergent such as an alkali metal dodecylsulphate such as sodium dodecylsulphate. Maintenance of a suitable concentration of the detergent, typically around 0.1%, during this step improves elimination of cellular polysaccharides and other contaminants.

BRIEF DESCRIPTION OF THE DRAWINGS

The invention will now be described in further detail, by way of example only, with reference to the following Examples and accompanying drawings.

FIG. 9 shows the results of silver stained polyacrylamide gel electrophoresis to assess elimination of protein (A) following high temperature ultrafiltration, and (B) following room temperature ultrafiltration.

DETAILED DESCRIPTION OF THE INVENTION

Figure 1:
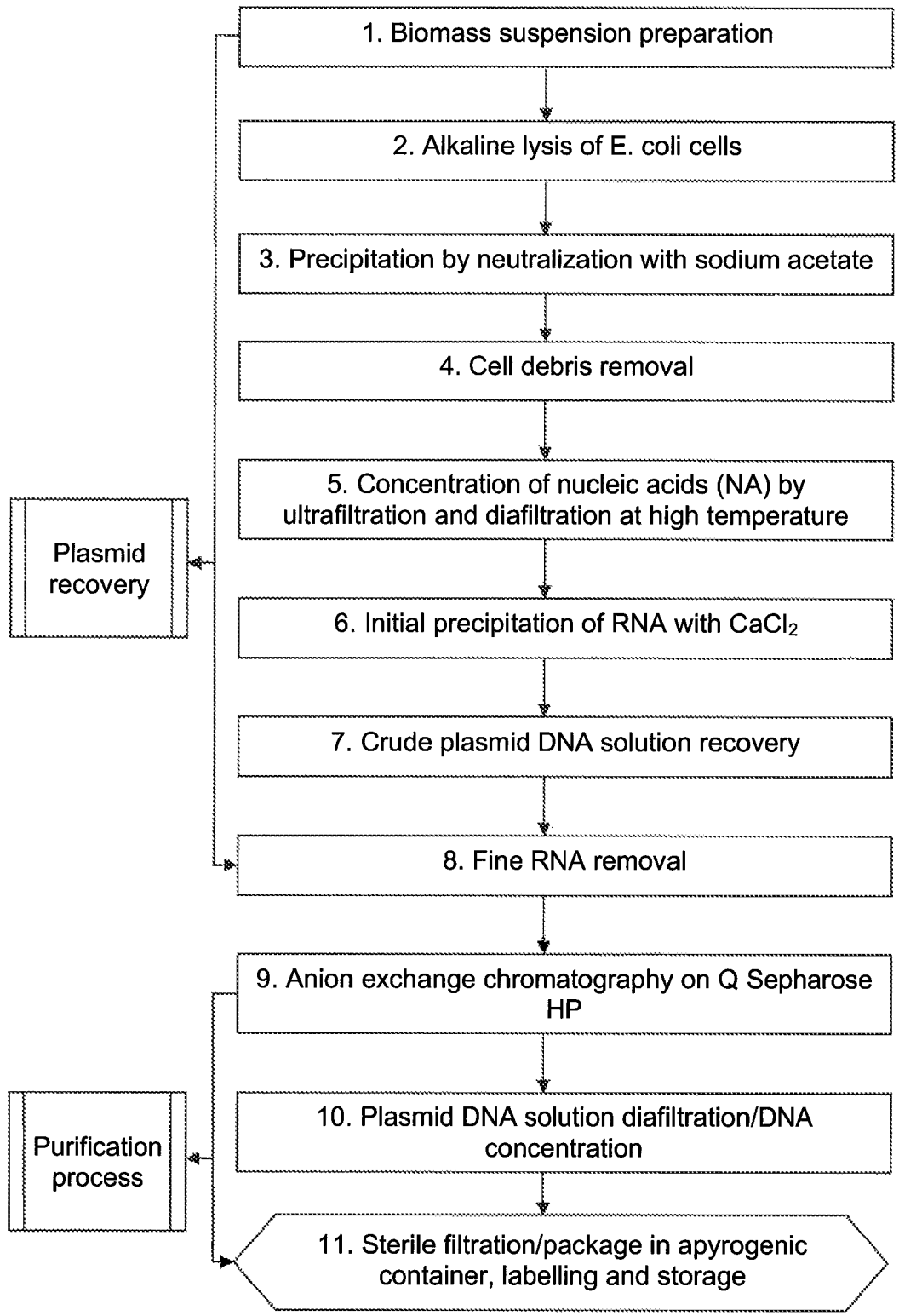
FIG. 1 shows a flow chart for plasmid purification according to the invention.

The method of purification of plasmid DNA presented below is capable of providing a number of advantages, including the extremely effective elimination of host cell protein and RNA prior to anion exchange chromatography step and the possibility to avoid the use of high volumes of organic solvents and exogenous animal derived proteins in the plasmid purification process. The method is adaptable to production for large-scale production of plasmid DNA, the purity of which meets therapeutic uses. The process speed is significantly higher compared to that of other industrially used pharmaceutical grade plasmid purification technologies.

EXAMPLE 1

1. Fermentation

*Escherichia coli* JM109 strain (ATCC 53323) with the following genotype: F' traD36 proA$^+$B$^+$ lacI$^q$ Δ(lacZ)M15/ e14$^-$ (McrA$^-$) Δ(lac-proAB) endA1 gyrA96 (Nal$^r$) thi-1 hsdR17 ($r_k^-m_k^+$) glnV44 reA1 recA1 or another suitable strain was transformed with the control 4276 bp size model plasmid (pMB1 replication origin, Km$^R$) that is to be produced, according to routine laboratory techniques. The resulting strain was characterized by the acquired resistance to kanamycin in addition to other phenotypic features described for a host strain. The presence of the transformed control plasmid in the transformed strain was tested by an alkaline extraction and gel electrophoresis. A transformant clone of the strain carrying the plasmid, which has been selected on a basis of the maximal production of control plasmid DNA with a correct restriction map, was used to prepare Master Cell Bank (MCB) and Working Cell Bank (WCB).

The fermentation process was performed as 100l batch fermentation in M9 modified medium containing 15 μg/ml antibiotic kanamycin in a BIOSTAT™ U-100 (B.Braun Biotech International GmbH, Melsungen, Germany) pilot scale fermenter. An aliquot of 1 ml from a frozen WCB tube was thawed at ambient temperature and quickly transferred into the 2l flask containing 1l of M9 modified medium: 20 g/l Na$_2$HPO$_4$, 4 g/l KH$_2$PO$_4$, 1 g/l NH$_4$Cl, 0.5 g/l NaCl, 10 g/l yeast extract, 2 ml/l glycerol, 1.5 g/l casamino acids, 1 mM MgSO$_4$, 15 μg/ml kanamycin, pH 7.3, for inoculate preparation. The flask was shaken at 37° C. and 200 rpm for 18 hours. The 1l of prepared inoculate with 4.0 AU optical density was transferred into a 100l Braun fermenter containing 80l of M9 modified medium: 20 g/l Na$_2$HPO$_4$, 4 g/l KH$_2$PO$_4$, 1 g/l NH₄Cl, 0.5 g/l NaCl, 10 g/l yeast extract, 2 ml/l glycerol, 1.5 g/l casamino acids, 1 mM MgSO₄, 15 µg/ml kanamycin, pH 7.3. The fermentation was processed under an automatic control of process parameters such as: temperature—37° C., $pO_2$—30% from saturation, pH 7.3, and stirring speed—100 rpm. After 5-7 hours of fermentation 20 l of 96° C. preheated medium were added to the fermenter and the temperature of the medium was increased by steam heating to 45° C. for thermal shock execution. The stirring speed was increased to 500 rpm and fermentation was continued until the stationary phase of cell proliferation was reached. The medium optical density was 10 AU. The fermentation broth was cooled and cells were harvested by centrifugation. The centrifuged cell biomass was weighted and washed once with suspension buffer: 25 mM Tris-HCl, pH8.0, 10 mM EDTA, 50 mM glucose. 900 g of washed cell paste was stored overnight on ice and submitted to plasmid DNA purification or frozen at −20° C. immediately after cell paste washing.

2. Plasmid DNA purification

A step-by-step flowchart and a detailed protocol for purification of control plasmid of *E.coli* cells are presented in FIG. 1. This example of process of plasmid DNA purification is elaborated below.

Step 1. Biomass suspension preparation: 250 g of *E.coli* cell paste was resuspended in suspending buffer ( 25 mM Tris-HCl, pH8.0, 10 mM EDTA, 50 mM glucose) at a ratio 1 gram of wet cell biomass/5 ml buffer and mixed to receive homogeneous suspension of cells.

Step 2. Alkaline lysis of *E.coli* cell: 1500 ml of resulting suspension from step 1 was added to 3125 ml of lysis buffer (0.2 M NaOH, 1% SDS, 0.1 M glucose) in a glass vessel and gently stirred with mixer for 5 minutes at room temperature.

Step 3. Precipitation by neutralization with sodium acetate: To the 4625 ml of lysed cell suspension, 2375 ml of 1.5M CH₃COONa, pH 4.8 solution was added and mixed for 20 minutes to form a uniform suspension with precipitated cellular debris. The precipitated cellular debris suspension was left for additional 20 minutes to form debris sedimentation.

Step 4. Cell debris removal: The cellular cell debris was submitted to centrifugation at 8000 rpm for 20 minutes at room temperature and 6520 ml of supernatant were collected into appropriate volume plastic bottle. Obtained nucleic acids solution was neutralised to pH 7.7+/−0.5 by adding 650 ml of 2.5 M Tris base solution. The final solution volume was 7170 ml. The NA solution was split into two portions and taken into hot and cold ultrafiltration processes in parallel.

Step 5. Nucleic acid (NA) concentration and diafiltration (in high temperature): 4000 ml of neutralized nucleic acid (NA) containing solution pH 7,7+/−0,5 were concentrated using three 100 kDa MWCO screen channel ultrafiltration Minisette Systems Cassettes with Omega Membrane (PALL FILTRON, USA) installed in Minisette Lab Tangential Flow System (PALL FILTRON, USA) ultrafiltration device. Total area of filtration was 0.21 sq. m. For NA concentration 30 kDa or 50 kDa, or 70 kDa, or 100 kDa MWCO screen channel cassettes with ultrafiltration membranes may be used. For plasmids less than 4000 bp in size the use of membranes up to 70 kDa MWCO is preferred in order to avoid the plasmid loss in the filtrate. The NA solution neutralization prior to concentration with Tris base solution up to pH 8.0 is preferable. The temperature of filtrated NA solution in the experiment was +40+/−2° C., solution supply speed was 1100+/−50 ml/min and the pressure in the ultrafiltration unit was 20+/−2 psi. Average filtrate flow speed was 120+/−5 ml/min.

The initial volume of neutralized NA solution was more than tenfold reduced by ultrafiltration up to 400 ml and 800 ml of 10 mM Tris-HCl, pH 8.0, 1 mM EDTA (TE buffer) were subsequently added to dilute the concentrated NA solution threefold. The NA diafiltration/concentration cycles were repeated two more times. The final diafiltrate was decanted, the system was flushed with TE buffer to collect a residual NA and flush solution was pooled with decanted diafiltrate. Resulting 600 ml of pool volume were taken into initial precipitation of RNA with CaCl₂.

Step 5. Nucleic acid (NA) concentration and diafiltration (in room temperature): 3170 ml of neutralized nucleic acid (NA) containing solution pH 7,7+/−0,5 were concentrated using the same technology as in ultrafiltration in the elevated temperature, except that ultrafiltration was performed at the room temperature. The NA solution neutralization prior to concentration with Tris base solution up to pH 8.0 prior to concentration is preferable. Ultrafiltration of NA solution was performed in the room temperature, since at the temperatures lower than 15-17° C. SDS/protein complex begins to precipitate out of solution, blocking this way the ultrafiltration membrane and significantly decreasing the process speed. Like in the previous example (high temperature) solution supply speed was 1100+/−50 ml/min and the pressure in the ultrafiltration unit was 20+/−2 psi. However, the average filtrate flow speed was only 58+/−5 ml/min. The initial volume of neutralized NA solution was more than tenfold reduced by ultrafiltration up to 315 ml and 630 ml of TE buffer were added to dilute concentrated NA solution volume up to threefold. The volume of NA solution was fourfold reduced by the next step of diafiltration. The diafiltration/concentration cycles were repeated twice. The final diafiltrate was decanted and the system was flushed with TE buffer to collect a residual NA that was pooled with decanted diafiltrate. 520 ml of pool volume was taken into initial precipitation of RNA with CaCl₂.

Step 6. Initial precipitation of RNA with CaCl₂: 600 ml of the NA solution resulting from the high temperature ultrafiltration procedure and 520 ml obtained in the room temperature ultrafiltration were adjusted to 0.2M CaCl₂ concentration by adding 150 ml and 130 ml, respectively, of 1M CaCl₂ solution at room temperature. Obtained suspension was maintained without stirring for approx. 60 minutes prior to subsequent centrifugation.

Step 7. Crude plasmid DNA solution recovery: The plasmid DNA containing supernatant after centrifugation at 8000 rpm for 20 minutes at room temperature was collected into the measuring cylinders. Both plasmid DNA samples were analysed in parallel by ion exchange chromatography on Q Sepharose HP. Chromatographic profiles and analysis results are presented in FIGS. 2 and 3.

Figure 2:
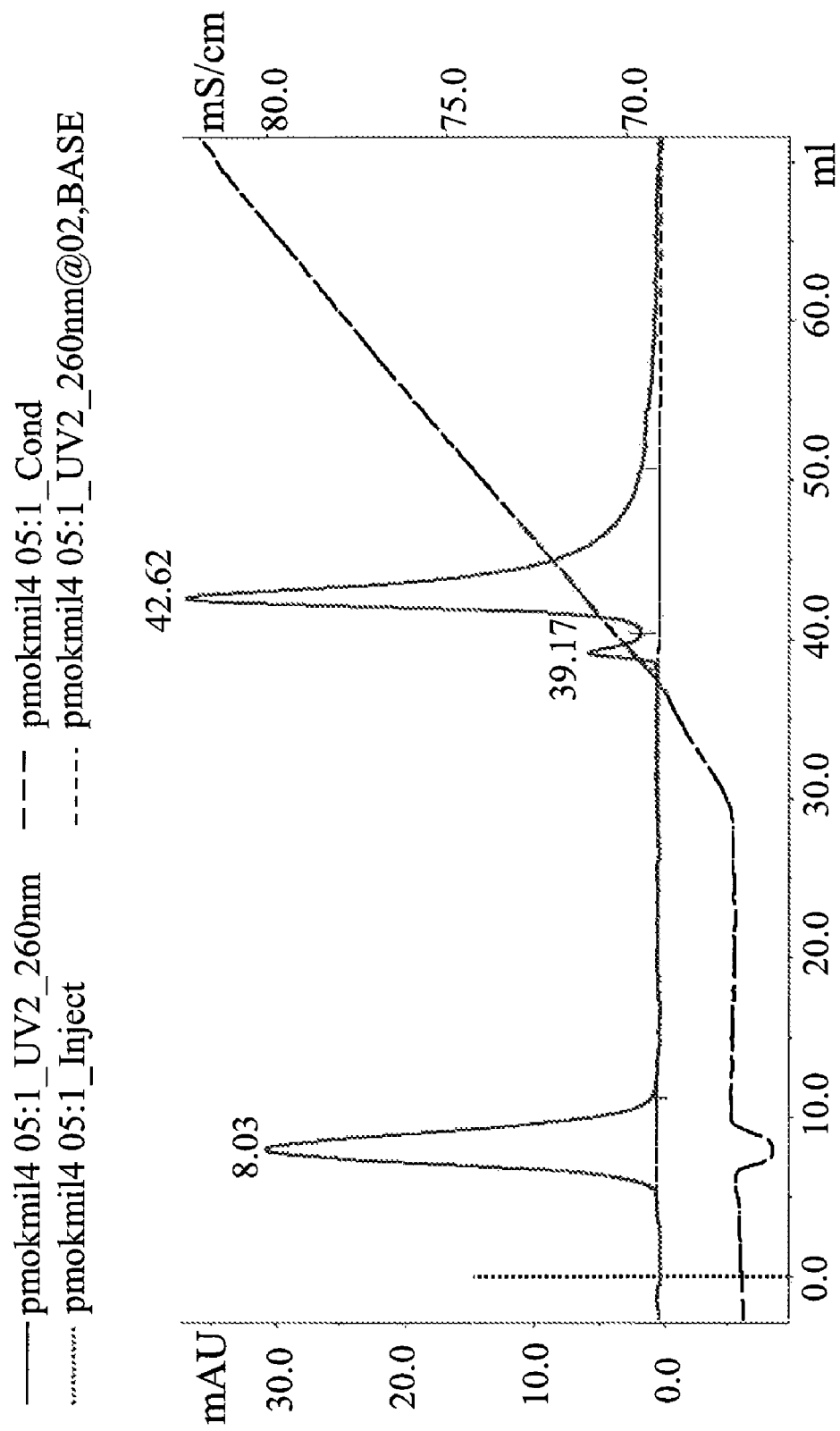
FIG. 2 shows a chromatographic profile and analysis of plasmid DNA following high temperature ultrafiltration in step 7 of the process.

FIG. 2 shows the chromatographic profile and analysis data of plasmid DNA containing supernatant after Step 7 using high temperature ultrafiltration: "mini-prep" of anion exchange chromatography on Q Sepharose HP XK-16 column; column volume—6 cm³, Buffer A—10 mM Tris, pH 8.0, 1 mM EDTA, 0.70M NaCl, λ=66 mS/cm, Buffer B—10 mM Tris, pH 8.0, 1 mM EDTA, 0.90 M NaCl, λ=84 mS/cm, flow rate—80 cm/h. Analysis of the chromatogram is as follows:

| No | Peak name | Ret (ml) | Area/Peak area ((volume) %) | Height mAU |
|---|---|---|---|---|
| 1 | RNA/polysaccharides | 8.03 | 42.08 | 29.210 |
| 2 | relaxed forms of plasmid DNA | 39.17 | 3.09 | 5.190 |
| 3 | supercoiled form of plasmid DNA | 42.62 | 54.83 | 35.420 |

Total area = 182.2107 mAU * ml
Area in evaluated peaks = 163.2895 mAU * ml
Ratio peak area/total area = 0.896158
Total peak width = 18.57 ml
Calculated from: pmokmil4 05:1_UV2_260 nm
Baseline: pmokmil4 05:1_UV2_260 nm@02, BASE
Peak rejection on:
Maximum number of peaks: 5
Current peak filter settings:
Maximum number of peaks: 20

Figure 3:
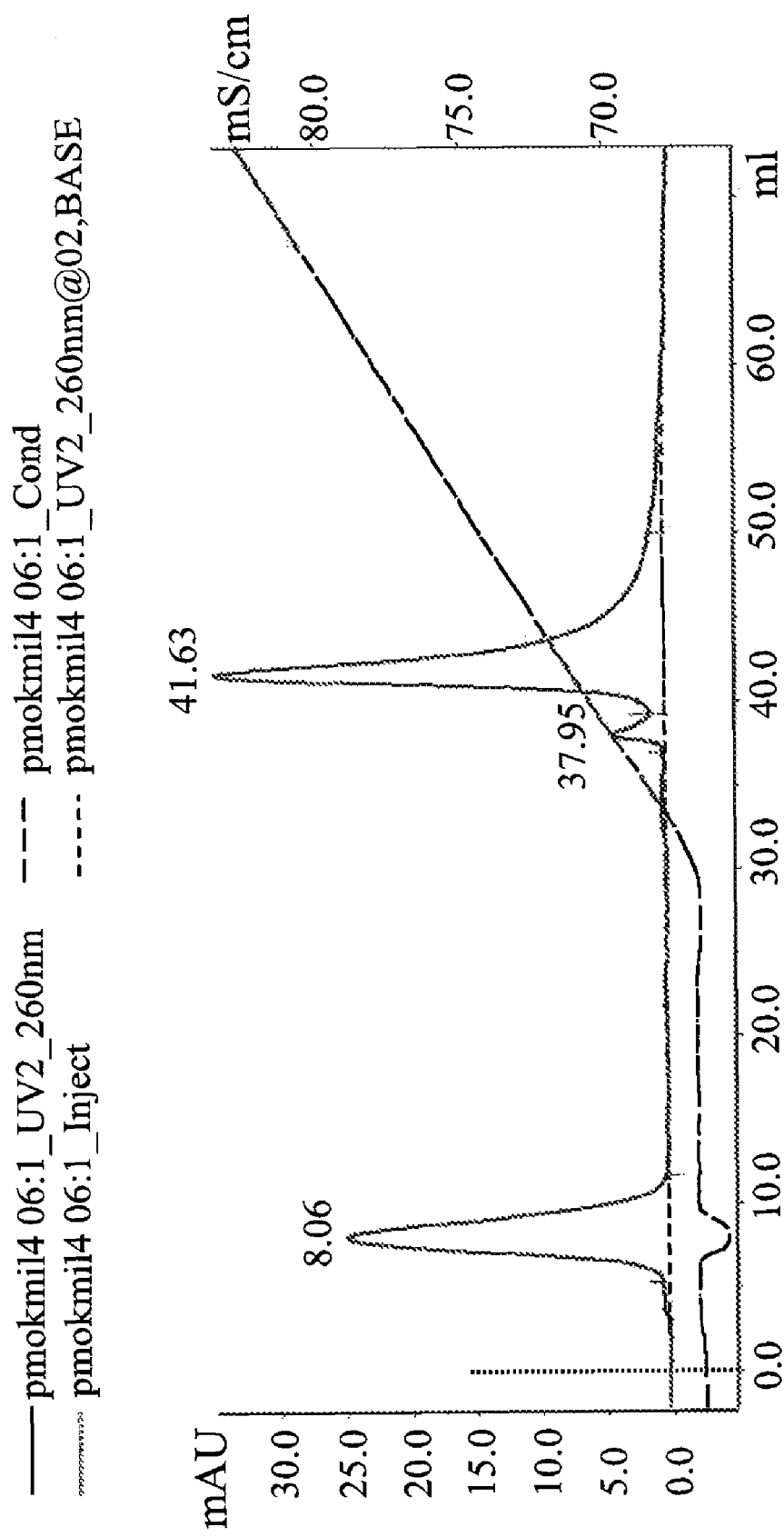
FIG. 3 shows a chromatographic profile and analysis of plasmid DNA following room temperature ultrafiltration in step 7 of the process.

FIG. 3 shows the chromatographic profile and analysis data of plasmid DNA containing supernatant after Step 7 using room temperature ultrafiltration: "mini-prep" of anion exchange chromatography on Q Sepharose HP XK-16 column; column volume—6 cm$^3$, Buffer A—10 mM Tris, pH 8.0, 1 mM EDTA, 0.70M NaCl, $\lambda$=66 mS/cm, Buffer B—10 mM Tris, pH 8.0, 1 mM EDTA, 0.90 M NaCl, $\lambda$=84 mS/cm, flow rate—80 cm/h. Analysis of the chromatogram is as follows:

| No | Peak name | Ret (ml) | Area/Peak area ((volume) %) | Height (mAU) |
|---|---|---|---|---|
| 1 | RNA/polysaccharides | 8.06 | 38.83 | 23.660 |
| 2 | relaxed forms of plasmid DNA | 37.95 | 2.89 | 3.830 |
| 3 | supercoiled form of plasmid DNA | 41.63 | 58.28 | 32.980 |

Total area = 148.9238 mAU * ml
Area in evaluated peaks = 141.9435 mAU * ml
Ratio peak area/total area = 0.953129
Total peak width = 19.55 ml
Calculated from: pmokmil4 06:1_UV2_260 nm
Baseline: pmokmil4 06:1_UV2_260 nm@02, BASE
Peak rejection on:
Maximum number of peaks: 5
Current peak filter settings:
Maximum number of peaks: 20

Step 8. Fine RNA removal (in high temperature): Before RNA removal, 725 ml of the plasmid DNA solution was twofold diluted up to 1450 ml with 10 mM Tris, pH 8.0, 1 mM EDTA, 0.70M NaCl, $\lambda$=65 mS/cm (loading buffer solution for anion exchange chromatography on Q Sepharose HP) and heated up to 50+/−2° C. Plasmid DNA containing solution was diafiltrated by using three 100 kDa MWCO screen channel ultrafiltration Minisette Systems Cassettes with Omega Membrane (PALL FILTRON, USA), installed in Minisette Lab Tangential Flow System (PALL FILTRON, USA) ultrafiltration device. Total filtration area was 0.21 sq. m. Loading buffer for anion exchange chromatography on Q Sepharose HP containing high NaCl concentration and high temperature were used for additional RNA removal by diafiltration of plasmid DNA solution. Diafiltration in the loading buffer solution for anion exchange chromatography on Q Sepharose HP facilitates the process transition to the following anion exchange chromatography step, since the composition of plasmid DNA buffer solution after diafiltration coincides with that used for equilibration of sorbent, this way any undesirable ion concentration effects in the sorbent may be avoided during the chromatography.

The initial volume of DNA solution was six times reduced up to 250 ml by ultrafiltration and loading buffer was added to restore the initial 1450 ml volume. Five cycles of diafiltration at +50+/−2° C. were performed. The diafiltrate was decanted and the system was flushed with buffer to collect a residual plasmid DNA that was pooled with decanted diafiltrate. 550 ml of pooled volume was taken into anion exchange chromatography on Q Sepharose HP. Plasmid DNA obtained in the high temperature diafiltration process was analysed by anion exchange chromatography on Q Sepharose HP. Chromatography profile and analysis results are presented in the FIG. 4.

Figure 4:
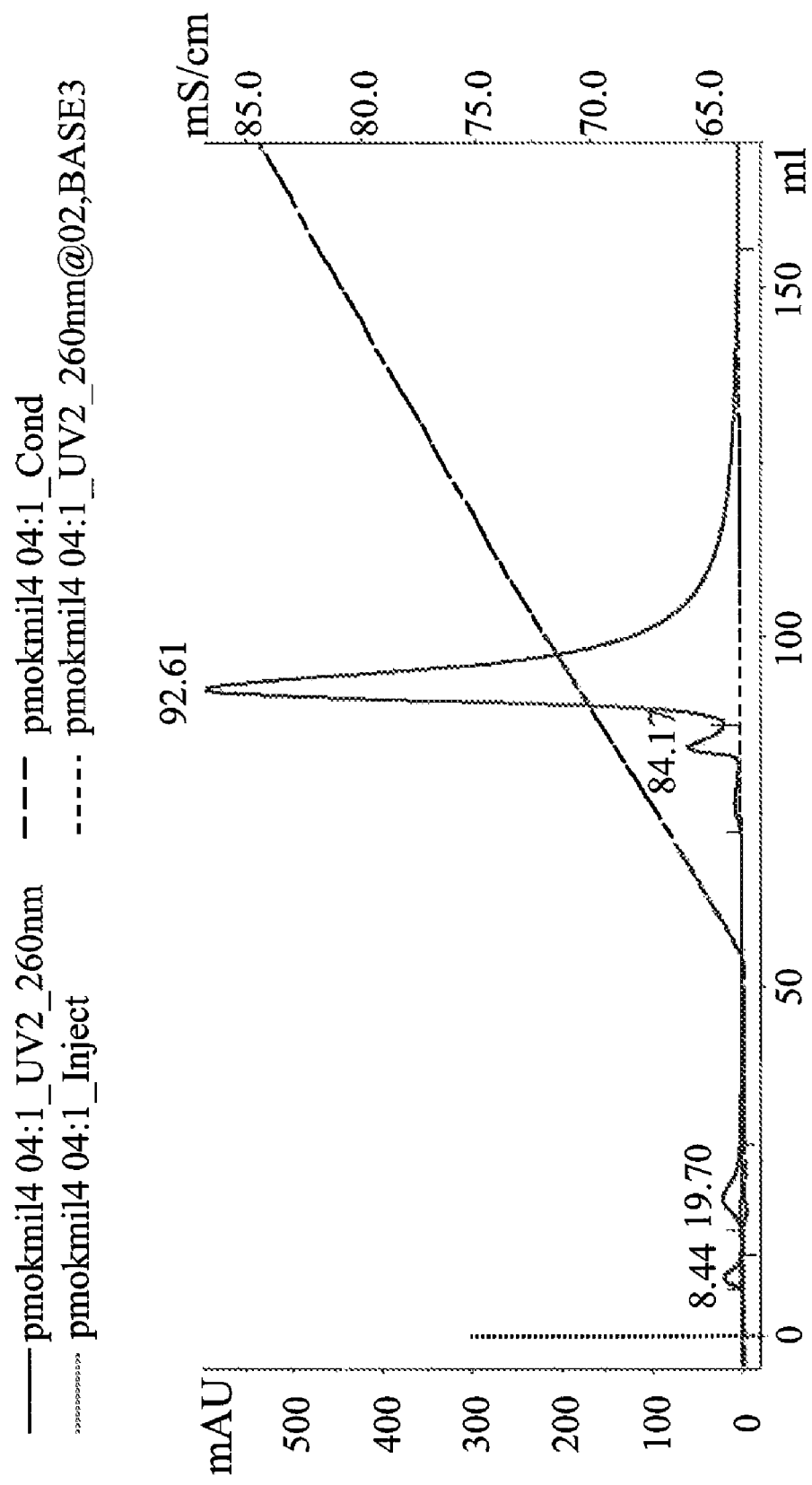
FIG. 4 shows a chromatographic profile and analysis of plasmid DNA after fine RNA removal using diafiltration at 50° C.

FIG. 4 shows the chromatographic profile and analysis data of plasmid DNA after Fine RNA removal (Step 8) using diafiltration at +50° C. temperature: "mini-prep" of anion exchange chromatography on Q Sepharose HP XK-16 column; column volume—16 cm$^3$, Buffer A—10 mM Tris, pH 8.0, 1 mM EDTA, 0.70M NaCl, $\lambda$=64 mS/cm, Buffer B—10 mM Tris, pH 8.0, 1 mM EDTA, 0.90 M NaCl, $\lambda$=84 mS/cm, flow rate—120 cm/h. Analysis of the chromatogram is as follows:

| No | Peak name | Ret (ml) | Area/Peak area ((volume) %) | Height (mAU) |
|---|---|---|---|---|
| 1 | polysaccharides | 8.44 | 0.84 | 17.720 |
| 2 | RNA | 19.70 | 2.11 | 19.690 |
| 3 | relaxed forms of plasmid DNA | 84.17 | 4.16 | 56.220 |
| 4 | supercoiled form of plasmid DNA | 92.61 | 92.89 | 569.890 |

Total number of detected peaks = 32
Total area = 4725.6799 mAU * ml
Area in evaluated peaks = 4704.8508 mAU * ml
Ratio peak area/total area = 0.995592
Total peak width = 100.47 ml
Calculated from: pMOKmIL4 04:1_UV2_260 nm
Baseline: pMOKmIL4 04:1_UV2_260 nm@02, BASE3
Peak rejection on:
Maximum number of peaks: 20
Current peak filter settings:
Maximum number of peaks: 20

Step 8. Fine RNA removal (in room temperature): Before RNA removal, 618 ml of the plasmid DNA solution was twofold diluted up to 1240 ml with 10 mM Tris, pH 8.0, 1 mM EDTA, 0.70M NaCl, $\lambda$=65 mS/cm (loading buffer solution for anion exchange chromatography on Q Sepharose HP) at room temperature. Plasmid DNA containing solution was diafiltrated using 100 kDa MWCO screen channel ultrafiltration Minisette Systems Cassettes with Omega Membrane (PALL FILTRON, USA), installed in Minisette Lab Tangential Flow System (PALL FILTRON, USA) ultrafiltration device. Loading buffer for anion exchange chromatography on Q Sepharose HP containing high NaCl concentration was used for additional RNA removal and diafiltration of plasmid DNA solution in the room temperature. The initial volume of DNA solution was six times reduced up to 200 ml by ultrafiltration and loading buffer was added to restore the initial 1200 ml volume. Five cycles of diafiltration at room temperature were performed. The diafiltrate was decanted and the system was flushed with buffer to collect a residual plasmid DNA that was pooled with decanted diafiltrate. 410 ml of pooled volume was taken into anion exchange chromatography on Q Sepharose HP. Plasmid DNA obtained in the room temperature diafiltration process was analysed by anion exchange chromatography on Q Sepharose HP. Chromatography profile and analysis results are presented in the FIG. 5.

Figure 5:
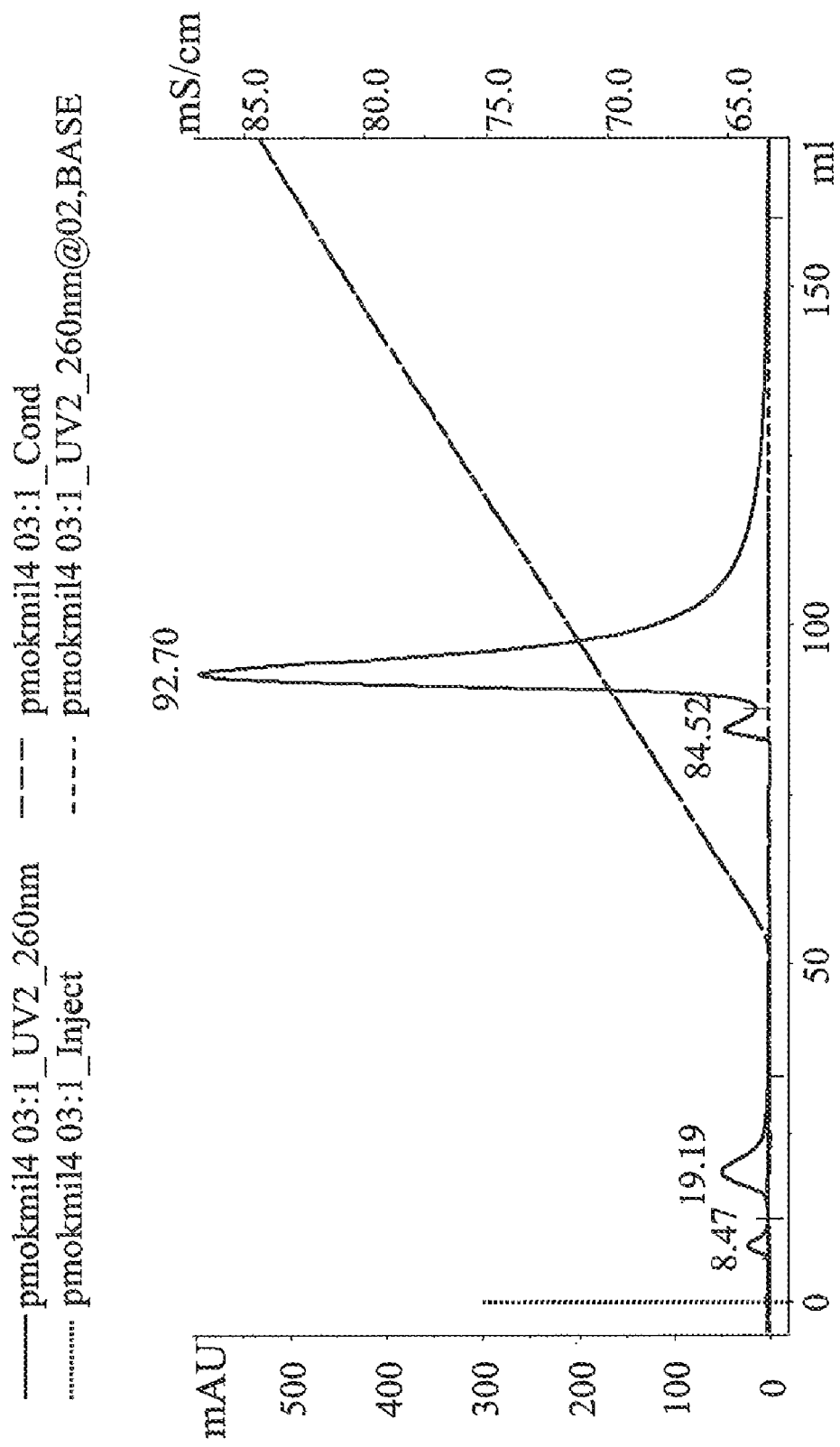
FIG. 5 shows a chromatographic profile and analysis of plasmid DNA after fine RNA removal using diafiltration at room temperature.

FIG. 5 shows the chromatographic profile and analysis data of plasmid DNA after Fine RNA removal (Step 8) using diafiltration at room temperature: "mini-prep" of anion exchange chromatography on Q Sepharose HP XK-16 column; column volume—16 cm$^3$, Buffer A—10 mM Tris, pH 8.0, 1 mM EDTA, 0.70M NaCl, λ=64 mS/cm, Buffer B—10 mM Tris, pH 8.0, 1 mM EDTA, 0.90 M NaCl, λ=84 mS/cm, flow rate—120 cm/h. Analysis of the chromatogram is as follows:

| No | Peak name | Ret (ml) | Area/Peak area ((volume) %) | Height (mAU) |
|---|---|---|---|---|
| 1 | polysaccharides | 8.47 | 1.05 | 21.780 |
| 2 | RNA | 19.19 | 5.26 | 47.310 |
| 3 | relaxed forms of plasmid DNA | 84.52 | 2.56 | 44.780 |
| 4 | supercoiled form of plasmid DNA | 92.70 | 91.13 | 573.800 |

Total area = 4825.3857 mAU * ml
Area in evaluated peaks = 4777.7240 mAU * ml
Ratio peak area/total area = 0.990123
Total peak width = 104.03 ml
Calculated from: pMOKmIL4 03:1_UV2_260 nm
Baseline: pMOKmIL4 03:1_UV2_260 nm@02, BASE
Peak rejection on:
Maximum number of peaks: 20
Current peak filter settings:
Maximum number of peaks: 20

Step 9. Anion exchange chromatography: 430 cm³ of Q Sepharose HP (Amersham Pharmacia Biotech, Sweden) in chromatographic column XK-50 (Amersham Pharmacia Biotech, Sweden) connected to AktaExplorer 100Air chromatographic system (Amersham Pharmacia Biotech, Sweden) were equilibrated with 10 mM Tris-HCl, pH 8.0, 1 mM EDTA, 0.70M NaCl, λ=65 mS/cm at a flow rate 46 cm/h until stable electric conductivity curve appeared in a monitor or recorder. Chromatographic process was controlled by Unicorn 3.00 software for Windows NT. Chromatographic purification of both plasmid sample preparations was performed using the same column at the same process parameters, by regenerating the sorbent before each chromatography. Both plasmid DNA solutions obtained in either high temperature or room temperature ultrafiltration were applied on an anion exchanger at a flow rate 46 cm/h. Elution of the adsorbed plasmid DNA with 8 columns volume length of a linear increasing gradient from 0.70M to 0.90M of NaCl in TE buffer, pH 8.0 at a flow rate 43 cm/h was carried out. Electric conductivity of a buffer solution was increased from 65 mS/cm to 84 mS/cm. Fractions of 45 ml were collected. Chromatographic fractions were analysed by 1% agarose gel electrophoresis. Fractions containing supercoiled plasmid DNA were pooled and the following final volumes plasmid DNA were obtained: 495 ml of plasmid DNA from high temperature ultrafiltration process and 450 ml of plasmid DNA from room temperature ultrafiltration process. Chromatographic profiles of both plasmid DNA solutions are presented in FIGS. 6 and 7.

Figure 6:
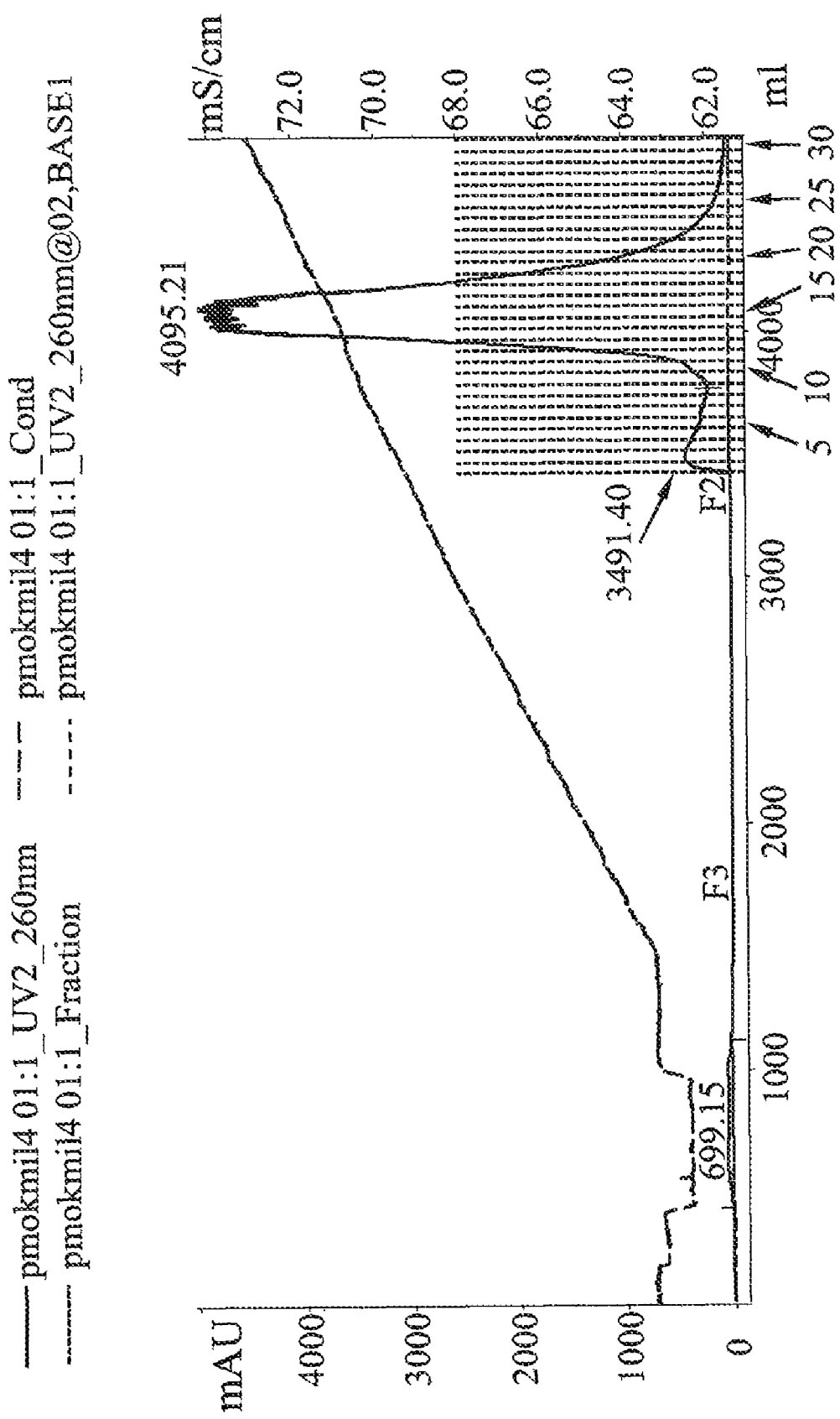
FIG. 6 shows a chromatographic profile and analysis of plasmid DNA after fine RNA removal using diafiltration at 50° C.

FIG. 6 shows the chromatographic profile and analysis data of plasmid DNA after Fine RNA removal (Step 8) using diafiltration at +50° C. temperature. Semi preparative anion exchange chromatography on Q Sepharose HP XK-50 column; column volume—430 cm³, Buffer A—10 mM Tris, pH 8.0, 1 mM EDTA, 0.70M NaCl, λ=66 mS/cm, Buffer B—10 mM Tris, pH 8.0, 1 mM EDTA, 0.90 M NaCl, λ=84 mS/cm, gradient flow rate—43 cm/h. Analysis of the chromatogram is as follows:

| No | Peak name | Ret (ml) | Area/Peak area ((volume) %) | Height (mAU) |
|---|---|---|---|---|
| 1 | RNA/polysaccharides | 699.15 | 1.51 | 49.930 |
| 2 | relaxed forms of plasmid DNA | 3491.40 | 6.44 | 396.430 |
| 3 | supercoiled form of plasmid DNA | 4095.21 | 92.05 | 4774.220 |

Total area = 1504886.5008 mAU * ml
Area in evaluated peaks = 1501728.1830 mAU * ml
Ratio peak area/total area = 0.997901
Total peak width = 2085.54 ml
Calculated from: pMOKmIL4 01:1_UV2_260 nm
Baseline: pMOKmIL4 01:1_UV2_260 nm@02, BASE1
Peak rejection on:
Maximum number of peaks: 25
Current peak filter settings:
Maximum number of peaks: 20

Figure 7:
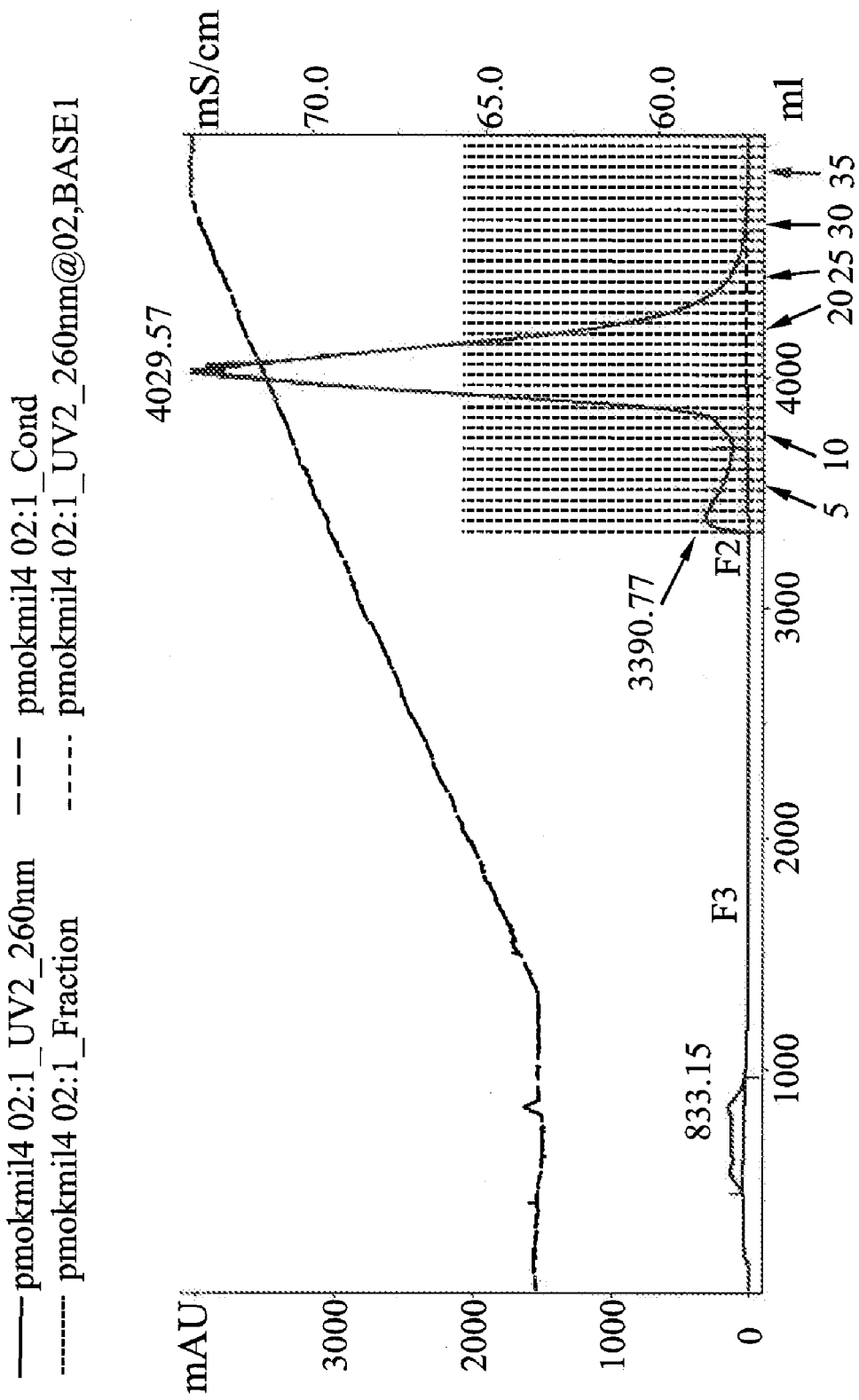
FIG. 7 shows a chromatographic profile and analysis of plasmid DNA after fine RNA removal using diafiltration at room temperature.

FIG. 7 shows the chromatographic profile and analysis data of plasmid DNA received after Fine RNA removal (Step 8) using diafiltration at room temperature. Semi preparative anion exchange chromatography on Q Sepharose HP XK-50 column; column volume—430 cm³, Buffer A—10 mM Tris, pH 8.0, 1 mM EDTA, 0.70M NaCl, λ=66 mS/cm, Buffer B—10 mM Tris, pH 8.0, 1 mM EDTA, 0.90 M NaCl, λ=84 mS/cm, gradient flow rate—43 cm/h. Analysis of the chromatogram is as follows:

| No | Peak name | Ret (ml) | Area/Peak area ((volume) %) | Height (mAU) |
|---|---|---|---|---|
| 1 | RNA/polysacharides | 833.15 | 3.02 | 110.160 |
| 2 | relaxed forms of plasmid DNA | 3390.77 | 6.38 | 294.960 |
| 3 | supercoil form of plasmid DNA | 4029.57 | 90.60 | 3890.120 |

Total area = 1083119.1953 mAU * ml
Area in evaluated peaks = 1083112.7265 mAU * ml
Ratio peak area/total area = 0.999994
Total peak width = 1874.38 ml
Calculated from: pmokmil4 02:1_UV2_260 nm
Baseline: pmokmil4 02:1_UV2_260 nm@02, BASE
Peak rejection on:
Maximum number of peaks: 25
Current peak filter settings:
Maximum number of peaks: 20

Step 10. Pooled plasmid DNA diafiltration and DNA concentration: The pooled plasmid DNA solutions from both plasmid preparations were diafiltrated in parallel using one 100 kDa MWCO screen channel ultrafiltration Minisette Systems Cassettes with Omega Membrane (PALL FILTRON, USA), installed in Minisette Lab Tangential Flow System (PALL FILTRON, USA) ultrafiltration device. 0.22 μm filtrated TE buffer was used for diafiltration of the plasmid DNA solutions. The initial volume of DNA solution was six times reduced by ultrafiltration and TE buffer was added to restore the initial volume. Three cycles of diafiltration were performed. Plasmid DNA diafiltrate volume in the last diafiltration cycle was reduced to obtain DNA concentration in the range of 4-5 mg/ml. Diafiltrate was decanted and the ultrafiltration system was flushed with TE buffer volume to collect the residual plasmid DNA and dilute DNA up to 1.8-2.2 mg/ml concentration.

Step 11. Bulk plasmid DNA preparation: The plasmid DNA solution at a final concentration was prepared and submitted to the sterile filtration into apyrogenic containers. Samples for quality control were taken. Containers were labelled with a description of the product lot #, volume, concentration, date of production and were stored frozen.

Figure 8:
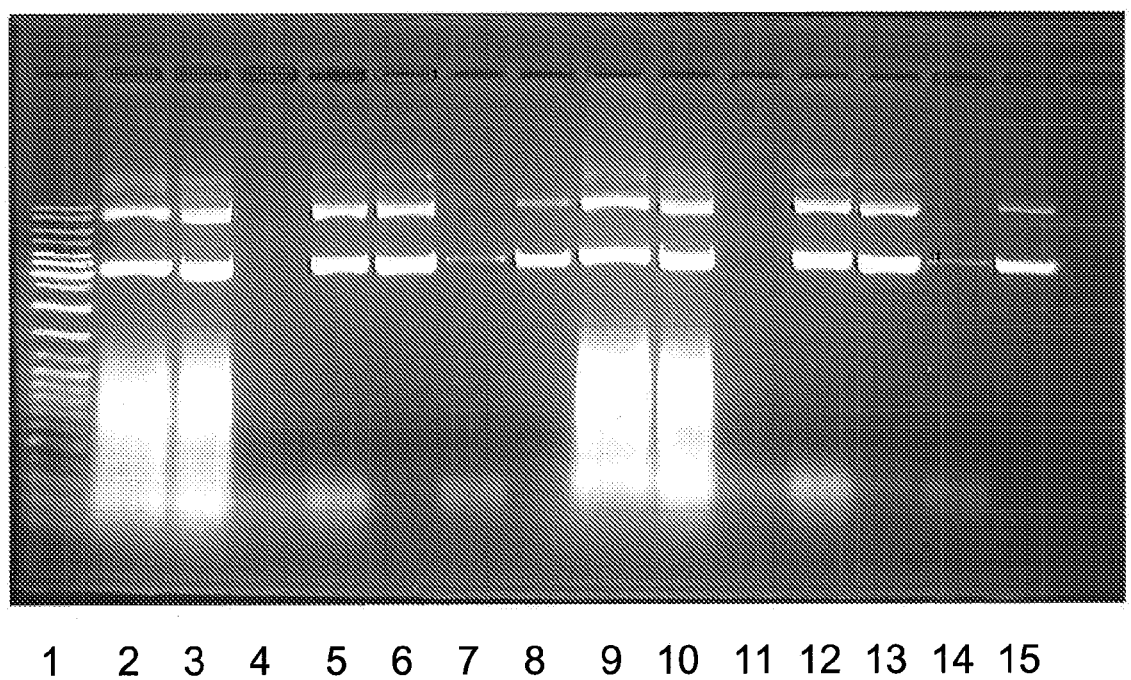
FIG. 8 shows the results of agarose gel electrophoresis on plasmid DNA purified in accordance with the invention.

Yields of test plasmid DNA after purification processes described above are presented in Table 1 for high temperature ultrafiltration and in Table 2 for room temperature ultrafiltration, RNA elimination course monitored by electrophoresis 1% agarose gel is presented in FIG. 8, host protein elimination course monitored by 10% SDS-PAGE, silver stained, is shown in the FIG. 9.

FIG. 8 shows a plasmid DNA purification course monitored by 1% agarose gel electrophoresis: lane 1—GeneRuler™ DNA Ladder Mix (#SM0331, Fermentas AB, Lithuania). Size of fragments (bp): 10000, 8000, 6000, 5000, 4000, 3500, 3000, 2500, 2000, 1500, 1200, 1031, 900, 800, 700, 600, 500, 400, 300, 200, 100.

Lanes 2-8 of the Figure represent high temperature ultrafiltration method: lane 2—Nucleic acid (NA) solution after Cell debris centrifugation step, lane 3—nucleic acid solution after NA concentration and diafiltration step, lane 4—filtrate after NA concentration and diafiltration, lane 5—NA solution after Initial precipitation of RNA with $CaCl_2$, lane 6—NA solution concentrate after Fine RNA removal step, lane 7—filtrate after Fine RNA removal step, lane 8—pooled plasmid DNA fractions after anion exchange chromatography. Lanes 9-15 represents room temperature ultrafiltration method: lane 9—Nucleic acid (NA) solution after Cell debris centrifugation step, lane 10—NA solution after NA concentration and diafiltration step, lane 11—filtrate after NA concentration and diafiltration, lane 12—NA solution after Initial precipitation of RNA with $CaCl_2$, lane 13—NA solution concentrate after Fine RNA removal step, lane 14—filtrate after Fine RNA removal step, lane 15—pooled plasmid DNA fractions after anion exchange chromatography.

FIG. 9 shows a protein elimination course during high and room temperature ultrafiltration plasmid DNA purification steps by silver stained 10% PAGE electrophoresis.

According to the Figure, panel A shows protein remaining on high temperature ultrafiltration; panel B shows protein remaining on room temperature ultrafiltration:

lane 1—nucleic acid solution after Cell debris centrifugation step, lane 2—concentrate of nucleic acid solution after Nucleic acid (NA) concentration and diafiltration step, lane 3—filtrate after Nucleic acid concentration and diafiltration step, lane 4—NA solution after Initial precipitation of RNA with $CaCl_2$ step, lane 5—filtrate after first diafiltration cycle during Fine RNA removal step, lane 6—filtrate after second diafiltration cycle, lane 7—filtrate after third diafiltration cycle, lane 8—filtrate after fifth diafiltration cycle, lane 9—pooled final filtrate after Fine RNA removal step, lane 10—final NA solution concentrate after Fine RNA removal step, lane 11—plasmid DNA after Anion exchange chromatography step, lane 12—Protein Molecular Weight Marker (#SM0431, Fermentas AB, Lithuania), kDa: 116.0, 66.2, 45.0, 35.0, 25.0, 18.4, 14.4.

It is evident from the presented data that temperature elevation from room temperature (20° C.) to 40° C. during the concentration of NA solution (Step 5) allowed to increase the ultrafiltration speed (average filtrate flow speed) about two times, i.e. from 58 to 120 ml/min in described experiment, while maintaining the same parameters of ultrafiltration process, namely, the NA solution supply speed (1100 m/min) and the pressure in the ultrafiltration unit (20 psi), and subsequently reduced the duration of concentration step at least twice.

Diafiltration and concentration of NA solution in TE buffer in step 5 when followed by subsequent $CaCl_2$ treatment allows the elimination of the majority of *E.coli* RNA, genomic DNA, cell proteins and large amounts of lipopolysaccharides. DNA electrophoretic analysis (lanes 3 and 5 in FIG. 8) and SDS PAGE analysis (lanes 2 and 4 in FIG. 9) as well as plasmid DNA chromatographic analysis (FIG. 2 and 3) indicate that concentration and diafiltration of NA solution increased the efficiency of the subsequent $CaCl_2$ treatment and efectively reduced the amount of contaminants. According to our data $CaCl_2$ treatment performed immediately after the acetate neutralisation step (Step 3, 4) is not that efficient and significantly higher amounts of contaminants of *E.coli* origin, such as different RNAs and their degradation products, are retained in the solution.

Figure 10:
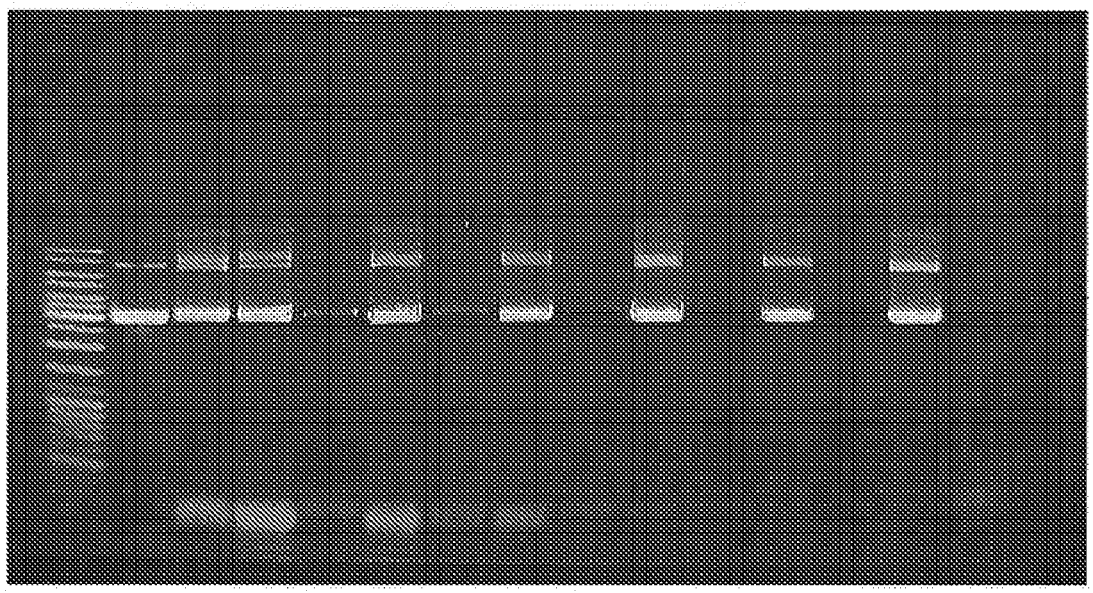
FIG. 10 shows the results of agarose gel electrophoresis analysis of diafiltrate and filtrate following fine RNA removal in the presence of 0.70M sodium chloride.

RNA diafiltration at 50° C. temperature and high (0, 70 M) NaCl concentration in step 8 allowed to reduce the amount of RNA/polysaccharide/protein contaminants to 1, 51% according to absorption at 260 nm, while the same step performed at the room temperature reduced the total amount of contaminating substances to 3, 01% according to semi preparative anion exchange chromatography data (FIG. 6, 7). Having in mind that usually polysaccharides constitute about 30% of RNA/polysaccharides peak (data from FIG. 4, 5) the final RNA amount in the plasmid DNA solution after Fine RNA removal step at 50° C. temperature constituted only about 1% from the total absorption at 260 nm. Fine RNA removal step carried out at room temperature was quite efficient as well, however, the final RNA amount constituted 2%. According to SDS-PAGE (FIG. 9) analysis results, the cell proteins remaining after the Initial precipitation of RNA with $CaCl_2$ step are effectively eliminated during diafiltration at step 8 (lanes 4 and 10). Moreover, experimental data indicate that diafiltration at 50° C. results in the lower amount of contaminating proteins than the same procedure performed at the room temperature (FIG. 9, lane 10). FIG. 10 shows the effectiveness of the fine RNA removal procedure, in the presence of 0.70M NaCl. The results shown are of electrophoretic analysis of diafiltrate and filtrate, obtained by filtering NA solution through screen channel 100 kDa MWCO: Lane 1—GeneRuler™ DNA Ladder Mix (#SM0331, Fermentas AB, Lithuania), lane 2—plasmid DNA standard, lane 3—initial RNA/DNA solution (NA solution), lanes 4 and 5—NA solution concentrate (retentate) and filtrate (permeate) after I diafiltration cycle, respectively, lanes 6 and 7—after II cycle, lanes 8 and 9—after III cycle, lanes 10 and 11—after IV cycle, lanes 12 and 13—after V cycle, lanes 14 and 15—pooled final NA solution (retentate) and filtrate (permeate). The results indicate that it is preferred to use several diafiltration cycles in the presence of high salt in order to obtain complete fine RNA removal.

Figure 11:
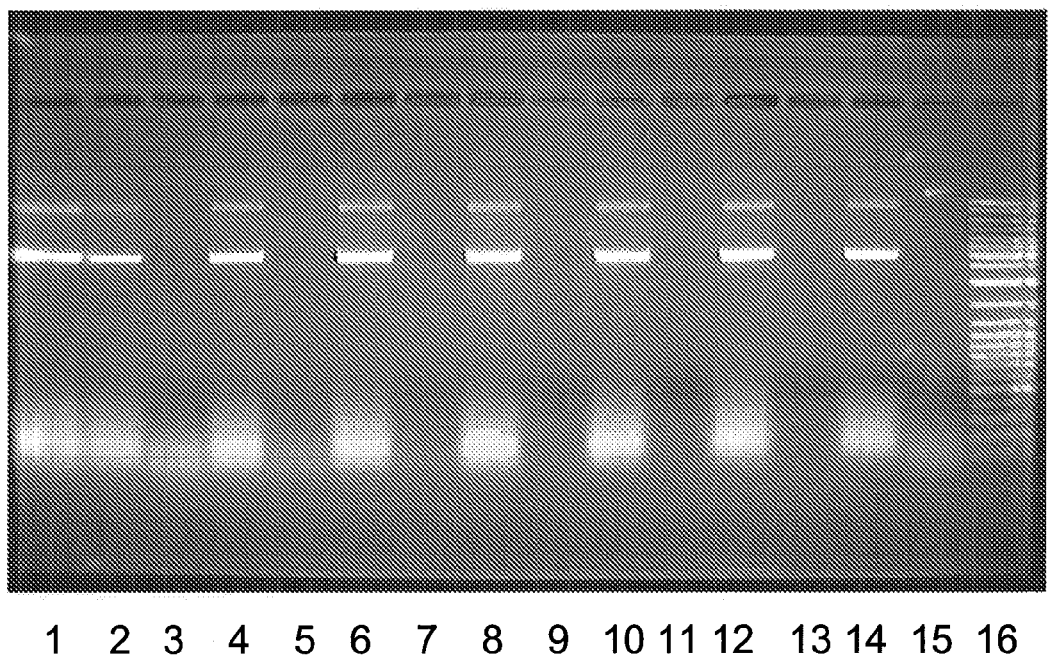
FIG. 11 shows the results of agarose gel electrophoresis analysis of diafiltrate and filtrate following fine RNA removal in the absence of 0.70M sodium chloride.

In contrast, FIG. 11 shows that fine RNA removal procedure without 0.70M NaCl is ineffective. The results shown are of electrophoretic analysis of diafiltrate and filtrate obtained by filtering NA solution through screen channel 100 kDa MWCO: Lane 1—initial RNA/DNA solution (NA solution), lanes 2 and 3—NA solution concentrate (retentate) and filtrate after I diafiltration cycle, respectively, lanes 4 and 5—after II cycle, lanes 6 and 7—after III cycle, lanes 8 and 9—after IV cycle, lanes 10 and 11—after V cycle, lanes 12 and 13—after VI cycle, lanes 14 and 15—pooled final NA solution (retentate) and filtrate (permeate), lane 16 GeneRuler™ DNA Ladder Mix (#SM0331, Fermentas AB, Lithuania). Without salt there is no low molecular weight RNA elimination during the process.

Figure 12:
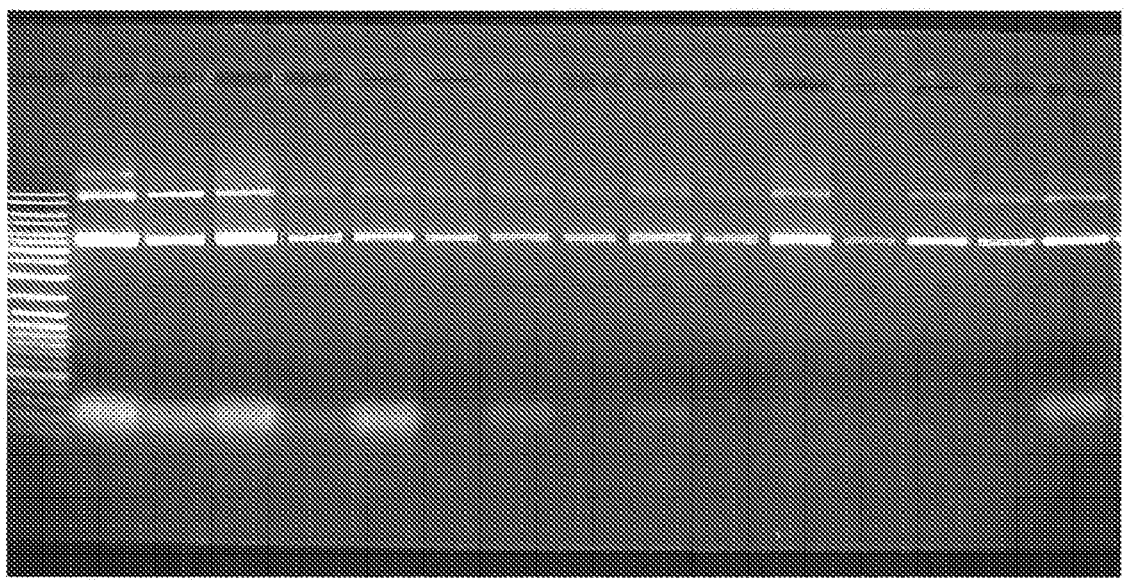
FIG. 12 shows the results of agarose gel electrophoresis analysis of diafiltrate and filtrate following fine RNA removal using a screen channel ultrafiltration unit.

FIG. 12 provides evidence that the fine RNA removal procedure in the presence of 0.70M NaCl proceeds without gel-layer formation when using a screen channel ultrafiltration unit. The results shown are of electrophoretic analysis of diafiltrate and filtrate, obtained by filtering NA solution through screen channel 300 kDa MWCO: Lane 1—GeneRuler™ DNA Ladder Mix (#SM0331, Fermentas AB, Lithuania), lane 2—initial RNA/DNA solution (NA solution), lanes 3 and 4 NA solution concentrate (retentate) and filtrate (permeate) after I diafiltration cycle, respectively, lanes 5 and 6—after II cycle, lanes 7 and 8—after III cycle, lanes 9 and 10—after IV cycle, lanes 11 and 12—after V cycle, lanes 13 and 14—after VI cycle, lanes 15 and 16—pooled final NA solution (retentate) and filtrate (permeate). When screen channel membranes are used with 300 kDa MWCO membrane instead of the open channel membranes as in WO98/05673, a large big plasmid DNA loss is observed in the permeate, due to the minimized formation of the gel layer on the membrane surface.

Anion exchange chromatography step 9 constitutes the final step of plasmid DNA purification process after which obtained plasmid DNA conforms in its characteristics to the requirements for therapeutic grade DNA (endotoxin concentration is already lower than 0, 10EU/µg DNA, tables 1 and 2). The diafiltration step used afterwards allows one to obtain the final preparation of purified plasmid DNA dissolved in the solution having the desired composition.

TABLE 1

Results of plasmid DNA purification using high temperature ultrafiltration method

| Purification Stage | Volume, ml | Endotoxin content, EU/ml | Total amount of nucleic acid, mg | RNA/DNA content | | DNA yield, % |
|---|---|---|---|---|---|---|
| | | | | RNA amount, mg | DNA amount, mg | |
| Cell debris removal, supernatant | 4000 | <1000000 | — | — | | |
| Nucleic acid (NA) concentration and diafiltration, concentrate of NA | 600 | >100000 | — | — | | |
| Initial precipitation of RNA with CaCl$_2$, supernatant | 725 | <1250 | 592 | 214 | 378 | 100 |
| Fine RNA removal | | | | | | |
| Concentrate | 550 | >800 | 377 | 6 | 371 | 98 |
| Diafiltrate | 7200 | <1250 | 208 | 208 | — | — |
| Anion exchange chromatography, pool of appropriate fractions | 495 | <50 | 317 | 0 | 317 | 84 |

TABLE 2

Results of plasmid DNA purification using room temperature ultrafiltration method

| Purification Stage | Volume, ml | Endotoxin content, EU/ml | Total amount of nucleic acid, mg | RNA/DNA content | | DNA yield, % |
|---|---|---|---|---|---|---|
| | | | | RNA amount, mg | DNA amount, mg | |
| Cell debris removal, supernatant | 3170 | <1000000 | — | — | | |
| Nucleic acid (NA) concentration and diafiltration, concentrate of NA | 520 | >100000 | — | — | | |
| Initial precipitation of RNA with CaCl$_2$, supernatant | 618 | <1250 | 449 | 151 | 298 | 100.0 |
| Fine RNA removal | | | | | | |
| Concentrate | 410 | <2500 | 287 | 7 | 280 | 94 |
| Diafiltrate | 6040 | <1250 | 105 | 144 | — | — |
| Anion exchange chromatography, pool of appropriate fractions | 450 | <50 | 252 | 0 | 252 | 84 |

EXAMPLE 2

1. Fermentation

Fermentation was performed as described in Example 1.

2. Plasmid DNA Purification

Figure 13:
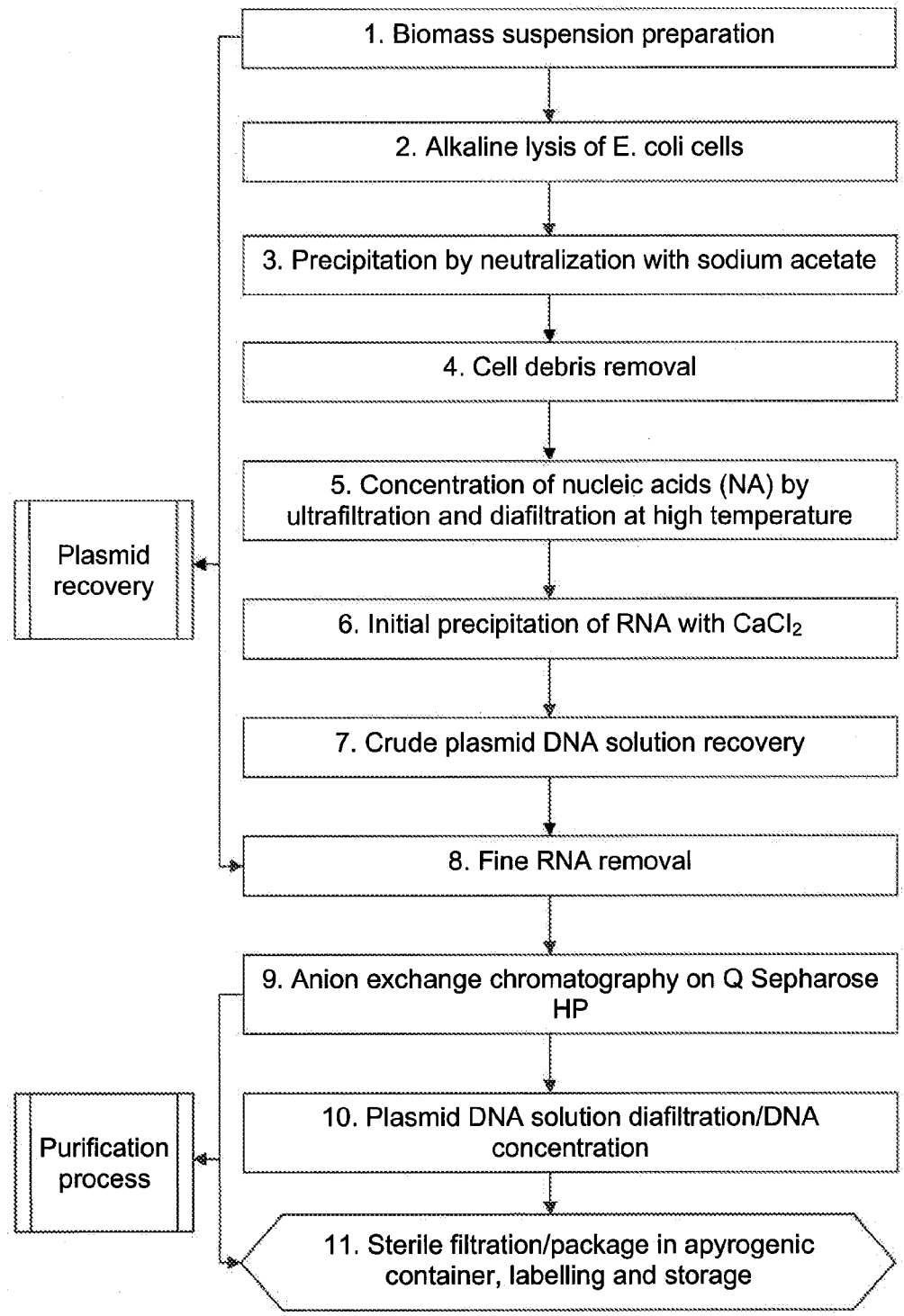
FIG. 13 shows a flow chart for plasmid purification according to a further embodiment of the invention.

A step-by-step flowchart and a detailed protocol for purification of control plasmid of E.coli cells are presented in FIG. 13. This example of process of plasmid DNA purification is elaborated below.

Step 1. Biomass suspension preparation: 200 g of E.coli cell paste was resuspended in suspending buffer (25 mM Tris-HCl, pH8.0, 10 mM EDTA, 50 mM glucose) at a ratio 1 gram of wet cell biomass/5 ml buffer and mixed to receive homogeneous suspension of cells.

Step 2. Alkaline lysis of E.coli cell: 1200 ml of resulting suspension from step 1 was added to 2500 ml of lysis buffer (0.2 M NaOH, 1% SDS, 0.1 M glucose) in a glass vessel and gently stirred with mixer for 5 minutes at room temperature.

Step 3. Precipitation by neutralization with sodium acetate: To the 3700 ml of lysed cell suspension, 1900 ml of 3M $CH_3COONa$, pH 4.8 solution was added and mixed for 10 minutes to form a uniform suspension with precipitated cellular debris.

Step 4. Cell debris removal: The cellular cell debris was submitted to centrifugation at 8000 rpm for 20 minutes at 18° temperature and 4880 ml of supernatant were collected into appropriate volume plastic bottle. Obtained nucleic acids solution was neutralised to pH 7.5+/−0.5 by adding 488 ml of 2.5 M Tris base solution and 240 ml of 5M NaOH. The final solution volume was 5608 ml. The NA solution was split into two equal portions and taken into ultrafiltration processes with 0.1% SDS and without 0.1% SDS in parallel.

Step 5. Nucleic acid (NA) concentration and diafiltration (with 0.1% SDS): 2804 ml of neutralized nucleic acid (NA) containing solution pH 7,5+/−0,5 were concentrated using two 100 kDa NMWL screen channel ultrafiltration Minisette Systems Cassettes with Omega Membrane (PALL FILTRON, USA) installed in Minisette Lab Tangential Flow System (PALL FILTRON, USA) ultrafiltration device. Total area of filtration was 0.14 sq. m. For NA concentration 30 kDa or 50 kDa, or 70 kDa, or 100 kDa NMWL screen channel cassettes with ultrafiltration membranes may be used. For plasmids less than 4000 bp in size the use of membranes up to 70 kDa NMWL is preferred in order to avoid the plasmid loss in the filtrate. The NA solution neutralization prior to concentration with Tris base and NaOH solutions up to pH 8.0+/−0.5 is preferable. The temperature of filtrated NA solution in the experiment was +40+/−2° C., pressure in the ultrafiltration unit was 20+/−2 psi. Average filtrate flow speed was 100+/−5 ml/min.

The initial volume of neutralized NA solution was more than tenfold reduced by ultrafiltration up to 280 ml and 560 ml of 10 mM Tris-HCl, pH 8.0, 1 mM EDTA, 0.1% SDS were subsequently added to dilute the concentrated NA solution threefold. The NA diafiltration/concentration cycles were repeated five times, than the NA diafiltration/concentration cycles were repeated three times, using 10 mM Tris-HCl, pH 8.0, 1 mM EDTA solution without 0.1% SDS (TE buffer). The final diafiltrate was decanted, the system was flushed with TE buffer to collect a residual NA and flush solution was pooled with decanted diafiltrate. Resulting 360 ml of pool volume were taken into initial precipitation of RNA with $CaCl_2$.

Step 5. Nucleic acid (NA) concentration and diafiltration (without 0.1% SDS): 2804 ml of neutralized nucleic acid (NA) containing solution pH 7,5+/−0,5 were concentrated using the same technology as in Step 5 (with 0.1% SDS), except that ultrafiltration was performed without 0.1% SDS. The NA solution neutralization prior to concentration with Tris base and NaOH solutions up to pH 8.0 is preferable. Ultrafiltration of NA solution was performed in 40+/−2° C. temperature. Like in the previous example (with 0.1% SDS) pressure in the ultrafiltration unit was 20+/−2 psi. Average filtrate flow speed was 80 ml/min. The initial volume of neutralized NA solution was more than tenfold reduced by ultrafiltration up to 280 ml and 560 ml of TE (10 mM Tris-HCl, 1 mM EDTA, pH8.0) buffer were added to dilute concentrated NA solution volume up to threefold. The volume of NA solution was fourfold reduced by the next step of diafiltration. The diafiltration/concentration cycles were repeated 6 times. The final diafiltrate was decanted and the system was flushed with TE buffer to collect a residual NA that was pooled with decanted diafiltrate. 360 ml of pool volume was taken into initial precipitation of RNA with $CaCl_2$.

Step 6. Initial precipitation of RNA with $CaCl_2$: 360 ml of the NA solution resulting from the ultrafiltration procedure with 0.1% SDS and 360 ml obtained in the ultrafiltration procedure without 0.1% SDS were adjusted to 0.2M $CaCl_2$ concentration by adding 90 ml of 1M $CaCl_2$ solution. Obtained suspension was maintained without stirring for approx. 30 minutes prior to subsequent centrifugation.

Step 7. Crude plasmid DNA solution recovery: The plasmid DNA containing supernatant after centrifugation at 8000 rpm for 20 minutes at room temperature was collected into the measuring cylinders. Both plasmid DNA samples were analysed in parallel by ion exchange chromatography on Q Sepharose HP. Chromatographic profiles and analysis results are presented in FIGS. 14 and 15.

Figure 14:
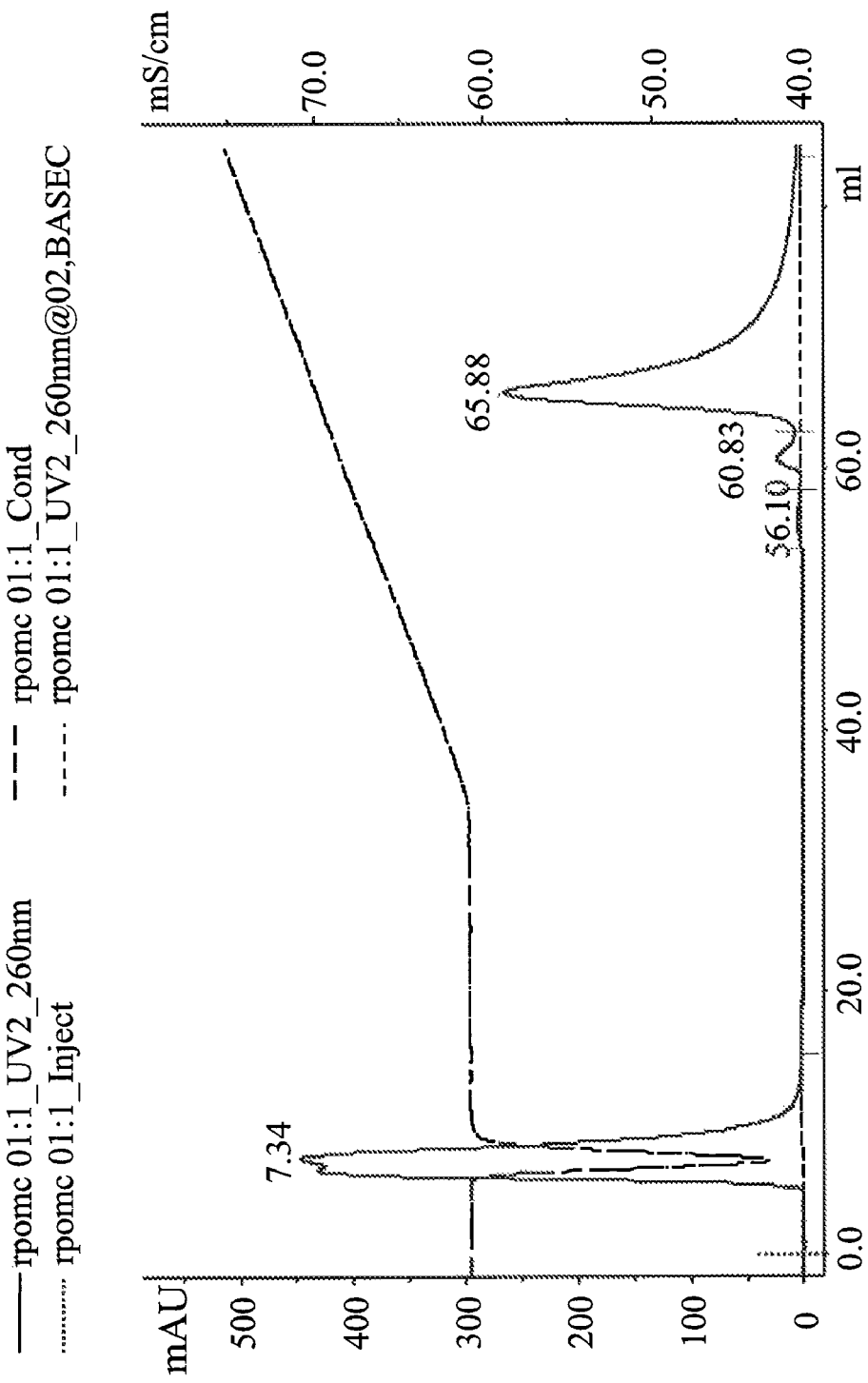
FIG. 14 shows a chromatographic profile and analysis of plasmid DNA following high temperature ultrafiltration with SDS in step 7 of the process.

FIG. 14 shows chromatographic profile and analysis data of plasmid DNA containing supernatant after Step 7 using high temperature ultrafiltration with 0.1% SDS: "mini-prep" of anion exchange chromatography on Q Sepharose HP HiTrap Q HP column; column volume—5 cm³, Buffer A—10 mM Tris, pH 8.0, 1 mM EDTA, 0.70M NaCl, λ=64 mS/cm, Buffer B—10 mM Tris, pH 8.0, 1 mM EDTA, 0.95 M NaCl, λ=84 mS/cm, flow rate—60 cm/h. Analysis of the chromatosgram is as follows:

| No | Peak name | Ret (ml) | Area (mAU * ml) | Area/Peak area ((volume)%) | Height (mAU) |
|---|---|---|---|---|---|
| 1 | RNA/Polysacharides | 7.34 | 305.3977 | 52.74 | 446.670 |
| 2 | Genomic DNA | 56.10 | 6.7491 | 0.27 | 2.300 |
| 3 | Relaxed form of plasmid DNA | 60.83 | 35.8755 | 1.45 | 21.310 |
| 4 | Supercoiled form of plasmid DNA | 65.88 | 127.0944 | 45.54 | 263.830 |

Figure 15:
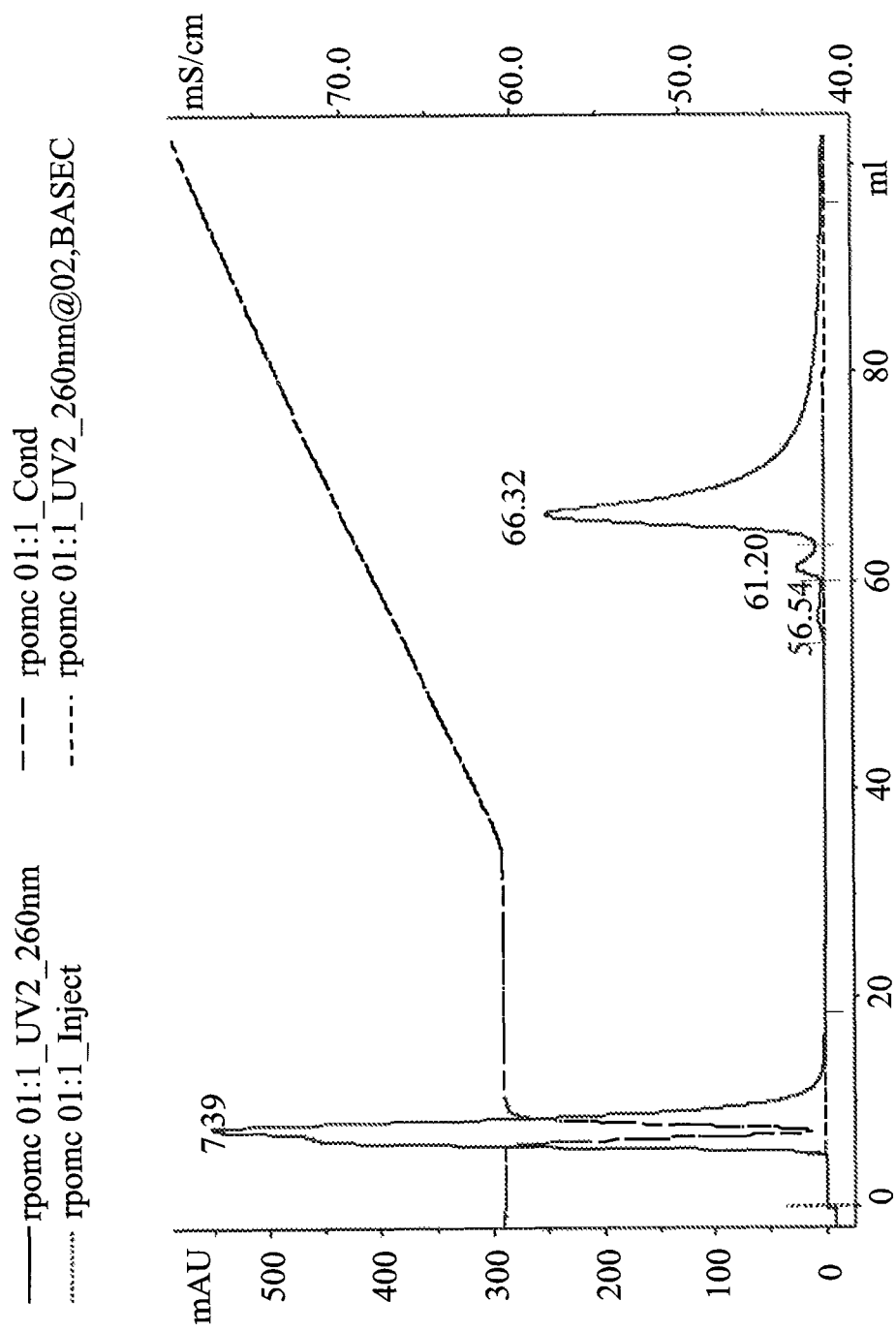
FIG. 15 shows a chromatographic profile and analysis of plasmid DNA following high temperature ultrafiltration without SDS in step 7 of the process.

Total area (mAU * ml) 2488.4278
Area in evaluated peaks (mAU * ml) 2475.1166
Ratio peak area/total area 0.994651
Total peak width (ml) 40.44
Calculated from rpomc po cacl2 su sds01:1_UV2_260 nm
Baseline rpomc po cacl2 su sds01:1_UV2_260 nm@02, BASEC
Peak rejection on
Maximum number of peaks ( ) 20
Current peak filter settings FIG. 15 shows the chromatographic profile and analysis data of plasmid DNA containing supernatant after Step 7 using high temperature ultrafiltration without: 0.1% SDS: "mini-prep" of anion exchange chromatography on Q Sepharose HP, HiTrap Q HPcolumn; column volume—5 cm³, Buffer A—10 mM Tris, pH 8.0, 1 mM EDTA, 0.70M NaCl, λ=64 mS/cm, Buffer B—10 mM Tris, pH 8.0, 1 mM EDTA, 0.95 M NaCl, λ=84 mS/cm, flow rate—60 cm/h. Analysis of the chromatogram is as follows:

| No | Peak name | Ret (ml) | Area (mAU * ml) | Area/Peak area ((volume)%) | Height (mAU) |
|---|---|---|---|---|---|
| 1 | RNA/Polysacharides | 7.39 | 1547.9908 | 55.41 | 551.230 |
| 2 | Genomic DNA | 56.54 | 17.5617 | 0.63 | 4.440 |
| 3 | Relaxed form of plasmid DNA | 61.20 | 44.1249 | 1.58 | 24.450 |
| 4 | Supercoiled form of plasmid DNA | 66.32 | 1184.1590 | 42.38 | 250.810 |

Total area (mAU * ml) 2825.9080
Area in evaluated peaks (mAU * ml) 2793.8365
Ratio peak area/total area 0.988651
Total peak width (ml) 55.99
Calculated from rpomc po Cacl2 be sds01:1_UV2_260 nm
Baseline rpomc po Cacl2 be sds01:1_UV2_260 nm@02, BASEC1
Peak rejection on
Maximum number of peaks ( ) 20
Current peak filter settings Step 8. Fine RNA removal (from sample following treatment in step 5 with 0.1% SDS): Before RNA removal, 435 ml of the plasmid DNA solution was twofold diluted up to 870 ml with 10 mM Tris, pH 8.0, 1 mM EDTA, 0.70M NaCl, λ=65 mS/cm (loading buffer solution for anion exchange chromatography on Q Sepharose HP) and heated up to 50+/−2° C. Plasmid DNA containing solution was diafiltered by using two 100 kDa NMWL screen channel ultrafiltration Minisette Systems Cassettes with Omega Membrane (PALL FILTRON, USA), installed in Minisette Lab Tangential Flow System (PALL FILTRON, USA) ultrafiltration device. Total filtration area was 0.14 sq. m. Loading buffer for anion exchange chromatography on Q Sepharose HP containing high NaCl concentration and high temperature were used for additional RNA removal by diafiltration of plasmid DNA solution. Diafiltration in the loading buffer solution for anion exchange chromatography on Q Sepharose HP facilitates the process transition to the following anion exchange chromatography step, since the composition of plasmid DNA buffer solution after diafiltration coincides with that used for equilibration of sorbent, this way any undesirable ion concentration effects in the sorbent may be avoided during the chromatography.

The initial volume of DNA solution was five times reduced up to 85 ml by ultrafiltration and loading buffer was added to restore the 500 ml volume. Five cycles of diafiltration at +50+/−2° C. were performed. The diafiltrate was decanted and the system was flushed with buffer to collect a residual plasmid DNA that was pooled with decanted diafiltrate. 205 ml of pooled volume was taken into hydrophobic chromatography on Phenyl Sepharose6FF. Plasmid DNA obtained in the diafiltration process with 0.1% SDS was analysed by anion exchange chromatography on Q Sepharose HP. Chromatography profile and analysis results are presented in the FIG. 16.

Figure 16:
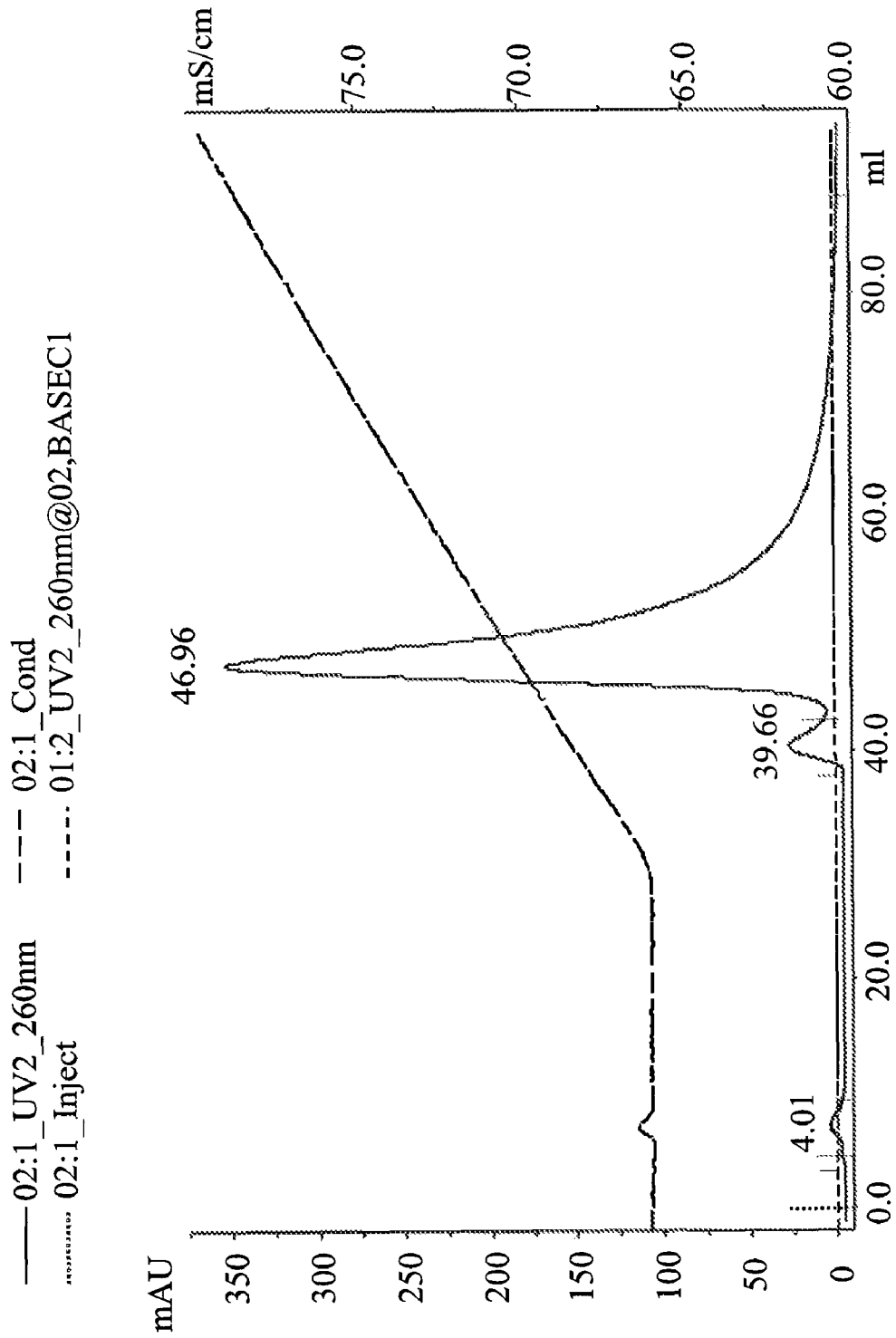
FIG. 16 shows a chromatographic profile and analysis of plasmid DNA after fine RNA removal using diafiltration at 50° C.

FIG. 16 shows the chromatographic profile and analysis data of plasmid DNA after Fine RNA removal (Step 8) using diafiltration at +50° C. temperature after concentration/diafiltration step with 0.1% SDS: "mini-prep" of anion exchange chromatography on Q Sepharose HP, HiTrap Q HP column; column volume—5 cm³, Buffer A—10 mM Tris, pH 8.0, 1 mM EDTA, 0.70M NaCl, λ=66 mS/cm, Buffer B—10 mM Tris, pH 8.0, 1 mM EDTA, 0.9 M NaCl, λ=84 mS/cm, flow rate—60 cm/h. Analysis of the chromatogram is as follows:

| No | Peak name | Ret (ml) | Area (mAU * ml) | Area/Peak area ((volume)%) | Height (mAU) |
|---|---|---|---|---|---|
| 1 | Polysacharides | 4.01 | 1.0646 | 0.04 | 1.460 |
| 2 | RNA | 6.63 | 19.0362 | 0.79 | 8.510 |
| 3 | Relaxed form of plasmid DNA | 39.66 | 86.3014 | 3.59 | 31.060 |
| 4 | Supercoiled form of plasmid DNA | 46.9 | 2300.2018 | 95.58 | 356.620 |

Figure 17:
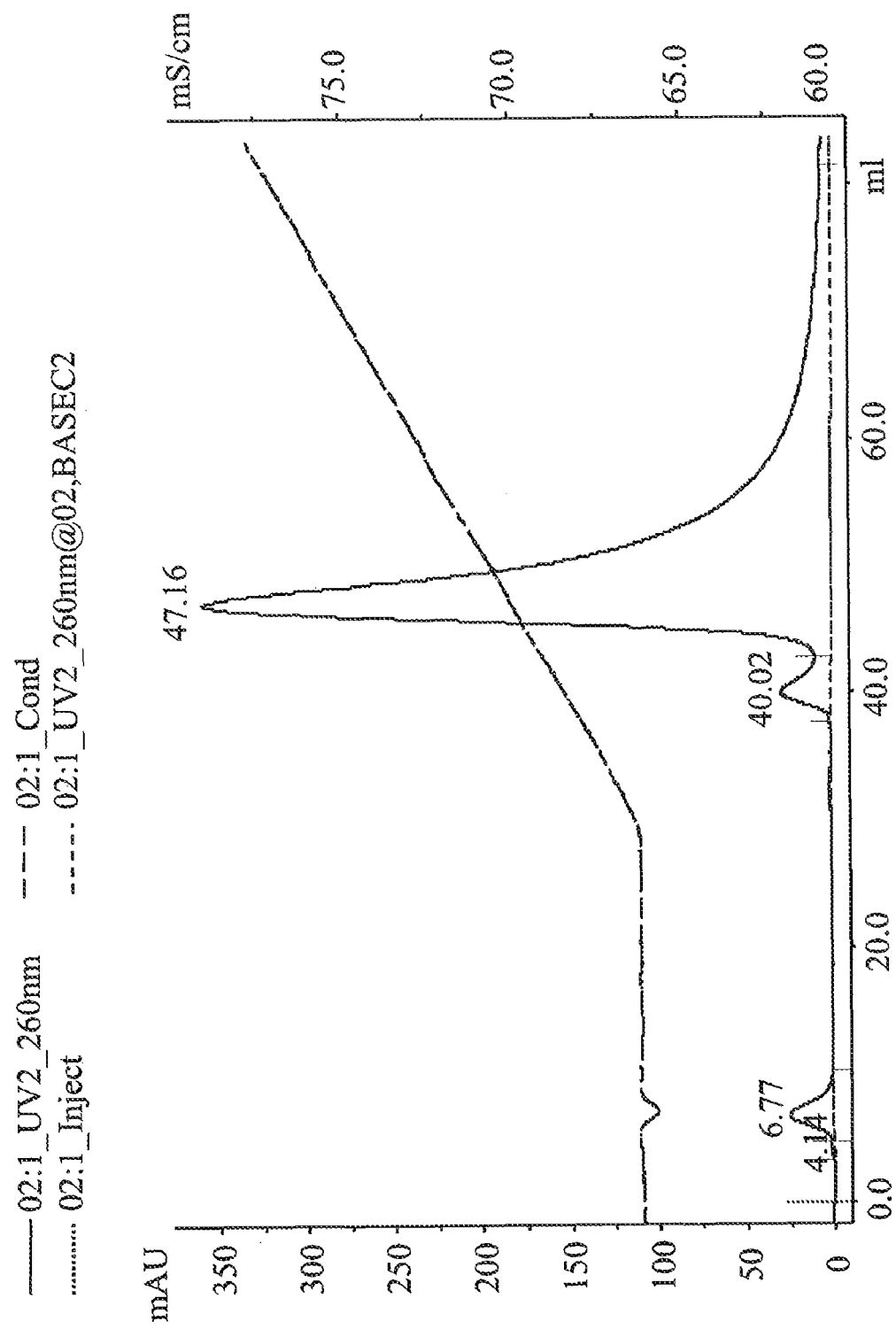
FIG. 17 shows a chromatographic profile and analysis of plasmid DNA after fine RNA removal using diafiltration without SDS.

Total area (mAU * ml) 2413.7948
Area in evaluated peaks (mAU * ml) 2406.6040
Ratio peak area/total area 0.997021
Total peak width (ml) 56.85
Calculated from mini prepas su sds 02:1_UV2_260 nm
Baseline mini prepas su sds 02:1_UV2_260 nm@02, BASEC1
Peak rejection on
Maximum number of peaks ( ) 20
Current peak filter settings Step 8. Fine RNA removal (from sample following treatment in step 5 without 0.1% SDS): Before RNA removal, 425 ml of the plasmid DNA solution was twofold diluted up to 850 ml with 10 mM Tris, pH 8.0, 1 mM EDTA, 0.70M NaCl, λ=65 mS/cm (loading buffer solution for anion exchange chromatography on Q Sepharose HP) and heated up to 50+/−2° C. Plasmid DNA containing solution was diafiltered using 100 kDa NMWL screen channel ultrafiltration Minisette Systems Cassettes with Omega Membrane (PALL FILTRON, USA), installed in Minisette Lab Tangential Flow System (PALL FILTRON, USA) ultrafiltration device. Total filtration area was 0.14 sq. m. Loading buffer for anion exchange chromatography on Q Sepharose HP containing high NaCl concentration and high temperature were used for additional RNA removal and diafiltration of plasmid DNA solution. The initial volume of DNA solution was five times reduced up to 85 ml by ultrafiltration and loading buffer was added up to 500 ml volume. Five cycles of diafiltration at high temperature were performed. The diafiltrate was decanted and the system was flushed with buffer to collect a residual plasmid DNA that was pooled with decanted diafiltrate. 205 ml of pooled volume was taken into hydrophobic chromatography on Phenyl Sepharose 6FF. Plasmid DNA obtained in the diafiltration process was analysed by anion exchange chromatography on Q Sepharose HP. Chromatography profile and analysis results are presented in the FIG. 17.

FIG. 16 shows the chromatographic profile and analysis data of plasmid DNA after Fine RNA removal (Step 8) using diafiltration at +50° C. temperature after concentration/diafiltration step with 0.1% SDS: "mini-prep" of anion exchange chromatography on Q Sepharose HP, HiTrap Q HP column; column volume—5 cm³, Buffer A—10 mM Tris, pH 8.0, 1 mM EDTA, 0.70M NaCl, λ=66 mS/cm, Buffer B—10 mM Tris, pH 8.0, 1 mM EDTA, 0.9 M NaCl, λ=84 mS/cm, flow rate—60 cm/h. Analysis of the chromatogram is as follows:

| No | Peak name | Ret (ml) | Area (mAU * ml) | Area/Peak area ((volume)%) | Height (mAU) |
|---|---|---|---|---|---|
| 1 | Polysacharides | 4.14 | 1.9249 | 0.08 | 1.840 |
| 2 | RNA | 6.77 | 53.6578 | 2.16 | 25.220 |
| 3 | Relaxed form of plasmid DNA | 40.02 | 75.9882 | 3.06 | 29.190 |
| 4 | Supercoiled form of plasmid DNA | 47.16 | 2353.6699 | 94.71 | 358.600 |

Total area (mAU * ml) 2503.5982
Area in evaluated peaks (mAU * ml) 2485.2408

-continued

| No | Peak name | Ret (ml) | Area (mAU * ml) | Area/Peak area ((volume)%) | Height (mAU) |
|---|---|---|---|---|---|

Ratio peak area/total area 0.992668
Total peak width (ml) 50.93
Calculated from mini prepas be sds02:1_UV2_260 nm
Baseline mini prepas be sds02:1_UV2_260 nm@02, BASEC2
Peak rejection on
Maximum number of peaks ( ) 20
Current peak filter settings Step 9. Hydrophobic chromatography 85 cm$^3$ of Phenyl Sepharose 6FF (Amersham Pharmacia Biotech, Sweden) in chromatographic column XK-26 (Amersham Pharmacia Biotech, Sweden) connected to AktaExplorer 100Air chromatographic system (Amersham Pharmacia Biotech, Sweden) were equilibrated with 10 mM Tris-HCl, pH 8.0, 1 mM EDTA, 0.70M NaCl, λ=66 mS/cm at a flow rate 56 cm/h until stable electric conductivity curve appeared in a monitor or recorder. Chromatographic process was controlled by Unicorn 3.00 software for Windows NT. Chromatographic purification of both plasmid sample preparations was performed using the same column at the same process parameters, by regenerating the sorbent before each chromatography. Both plasmid DNA solutions obtained in either ultrafiltration with 0.1% SDS or ultrafiltration without 0.1% SDS were applied on Phenyl Sepharose 6FF at a flow rate 56 cm/h. Plasmid DNA was flowed through and collected. Final volumes plasmid DNA were obtained: 203 ml of plasmid DNA from ultrafiltration process with 0.1% SDS and 203 ml of plasmid DNA from ultrafiltration process without 0.1% SDS. Chromatographic profiles of both plasmid DNA solutions are presented in FIGS. 18 and 19.

Figure 18:
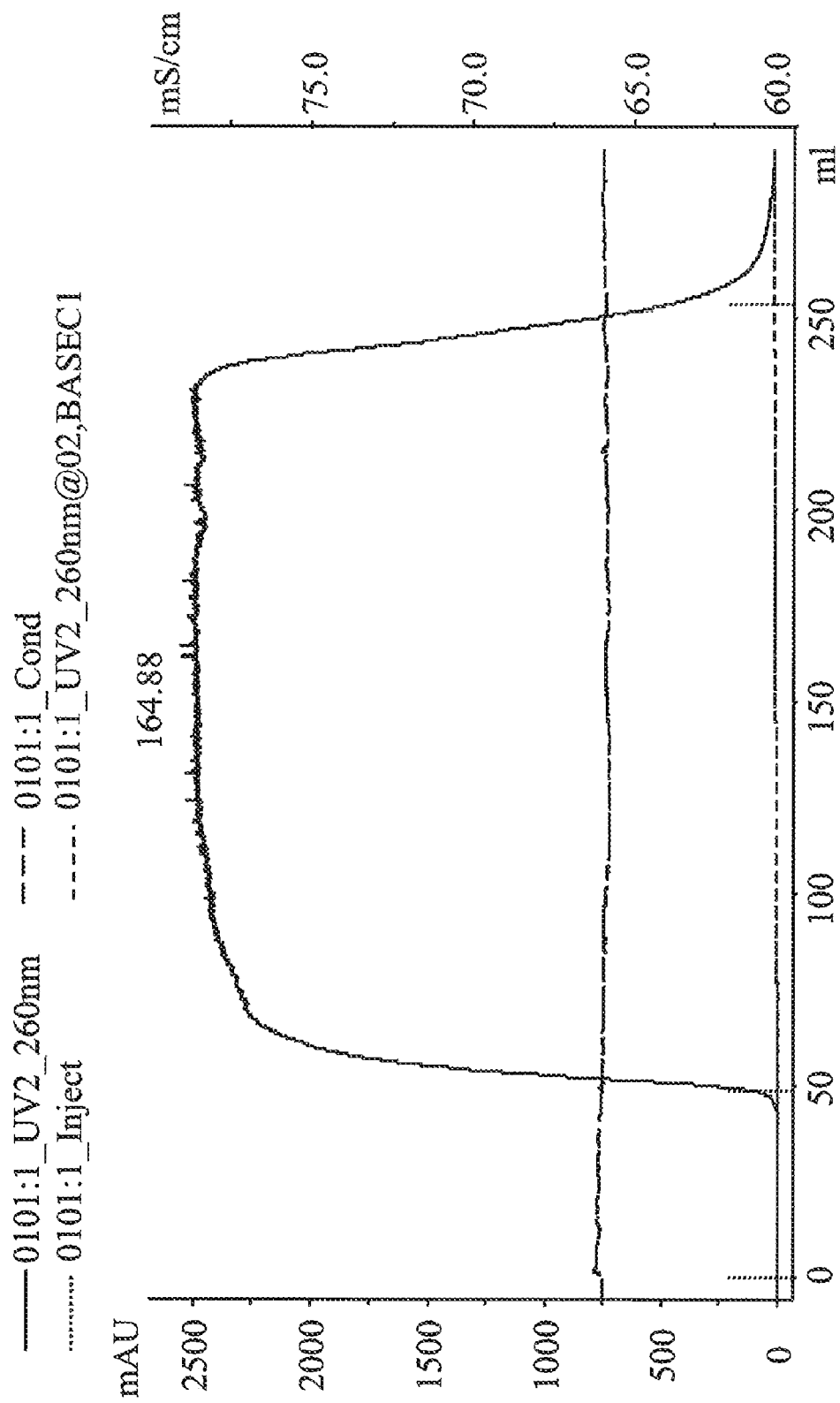
FIG. 18 shows a chromatographic profile and analysis of plasmid DNA after fine RNA removal using diafiltration with SDS.

FIG. 18 shows he chromatographic profile and analysis data of plasmid DNA after Fine RNA removal (Step 8) using diafiltration at +50° C. temperature, NA concentration/diafiltration (Step6) with 0.1% SDS. Hyrophobic chromatography on Phenyl Sepharose 6FF, XK-26 column; column volume—85 cm$^3$, Buffer A—10 mM Tris, pH 8.0, 1 mM EDTA, 0.70M NaCl, λ=66 mS/cm, flow rate 56 cm/h. Analysis of the chromatogram is as follows:

| No | Peak name | Ret (ml) | Area (mAU * ml) | Area/Peak area ((volume)%) | Height (mAU) |
|---|---|---|---|---|---|
| 1 | RNA and plasmid DNA | 164.88 | 467276.1527 | 100.00 | 2550.710 |

Total area (mAU * ml) 471872.4674
Area in evaluated peaks (mAU * ml) 467276.1527
Ratio peak area/total area 0.990259
Total peak width (ml) 202.79
Calculated from Phenyl Sepharose 0101:1_UV2_260 nm
Baseline Phenyl Sepharose 0101:1_UV2_260 nm@02, BASEC1
Current peak filter settings
Maximum number of peaks ( ) 20

Figure 19:
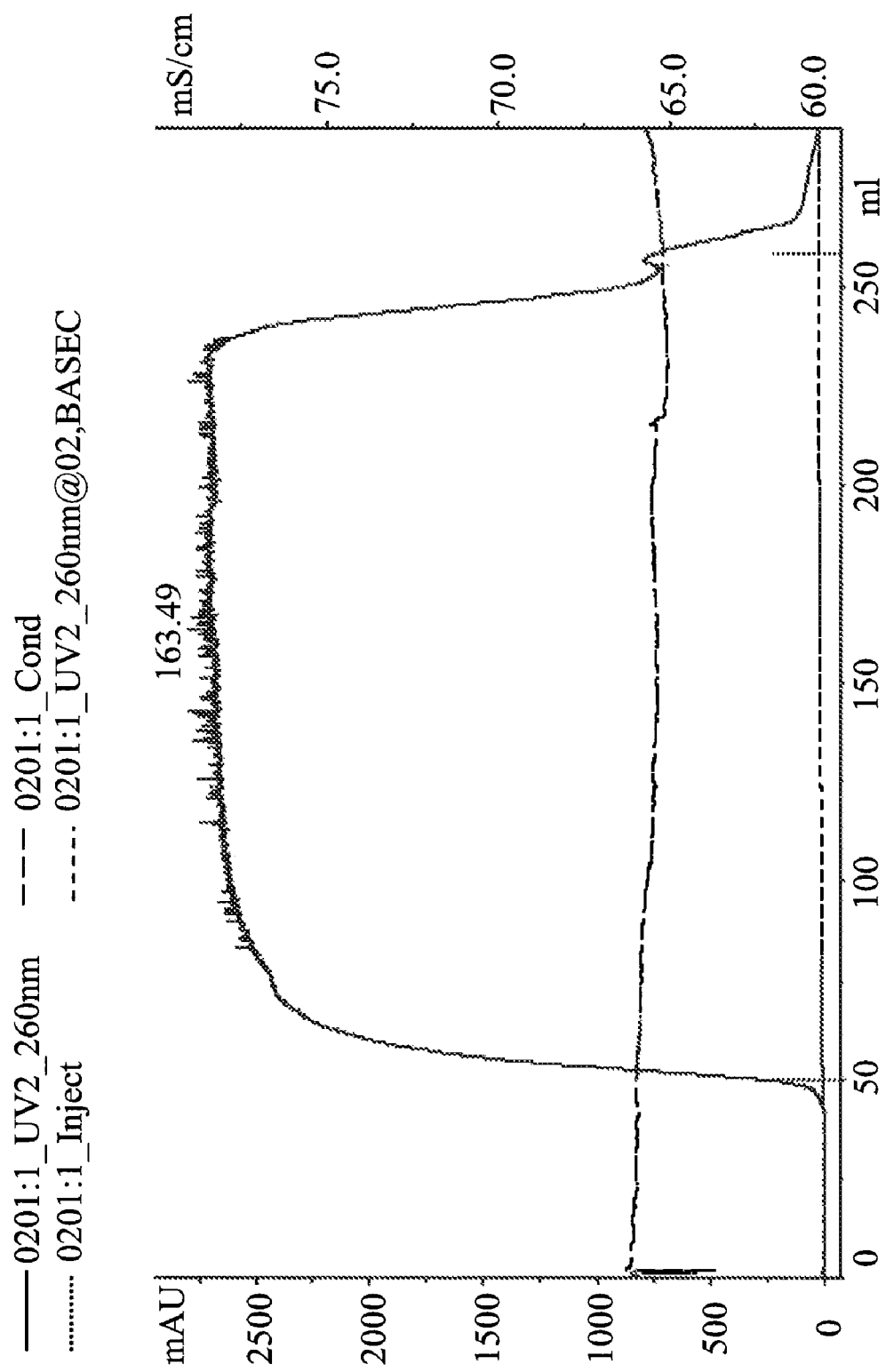
FIG. 19 shows a chromatographic profile and analysis of plasmid DNA after fine RNA removal using diafiltration without SDS.

FIG. 19 shows the chromatographic profile and analysis data of plasmid DNA after Fine RNA removal (Step 8) using diafiltration at +50° C. temperature, NA concentration/diafiltration (Step6) without 0.1% SDS. Hydrophobic chromatography on Phenyl Sepharose 6FF, XK-26 column; column volume—85 cm$^3$, Buffer A—10 mM Tris, pH 8.0, 1 mM EDTA, 0.70M NaCl, λ=66 mS/cm, flow rate 56 cm/h. Analysis of the chromatogram is as follows:

| No | Peak name | Ret (ml) | Area (mAU * ml) | Area/Peak area ((volume)%) | Height (mAU) |
|---|---|---|---|---|---|
| 1 | RNA and plasmid DNA | 163.49 | 503668.7017 | 100.00 | 2788.110 |

Total area (mAU * ml) 511791.8029
Area in evaluated peaks (mAU * ml) 503668.7017
Ratio peak area/total area 0.984128
Total peak width (ml) 203.57
Calculated from Phenyl Sepharose 0201:1_UV2_260 nm
Baseline Phenyl Sepharose 0201:1_UV2_260 nm@02, BASEC
Current peak filter settings
Maximum number of peaks ( ) 20

Step 10. Anion exchange chromatography: 125 cm$^3$ of Q Sepharose HP (Amersham Pharmacia Biotech, Sweden) in chromatographic column XK-26 (Amersham Pharmacia Biotech, Sweden) connected to AktaExplorer 100Air chromatographic system (Amersham Pharmacia Biotech, Sweden) were equilibrated with 10 mM Tris-HCl, pH 8.0, 1 mM EDTA, 0.70M NaCl, λ=66 mS/cm at a flow rate 45 cm/h until stable electric conductivity curve appeared in a monitor or recorder. Chromatographic process was controlled by Unicorn 3.00 software for Windows NT. Chromatographic purification of both plasmid sample preparations was performed using the same column at the same process parameters, by regenerating the sorbent before each chromatography. Both plasmid DNA solutions obtained in either ultrafiltration with 0.1% SDS or ultrafiltration without 0.1% SDS were applied on an anion exchanger at a flow rate 45 cm/h. Elution of the adsorbed plasmid DNA with 10columns volume length of a linear increasing gradient from 0.70M to 0.95M of NaCl in TE buffer, pH 8.0 at a flow rate 45 cm/h was carried out. Electric conductivity of a buffer solution was increased from 66 mS/cm to 84 mS/cm. Fractions of 20 ml were collected. Chromatographic fractions were analysed by 1% agarose gel electrophoresis. Fractions containing supercoiled plasmid DNA were pooled and the following final volumes plasmid DNA were obtained: 120 ml of plasmid DNA from ultrafiltration process with 0.1% SDS and 120 ml of plasmid DNA from ultrafiltration process without 0.1% SDS. Chromatographic profiles of both plasmid DNA solutions are presented in FIGS. 20 and 21.

Figure 20:
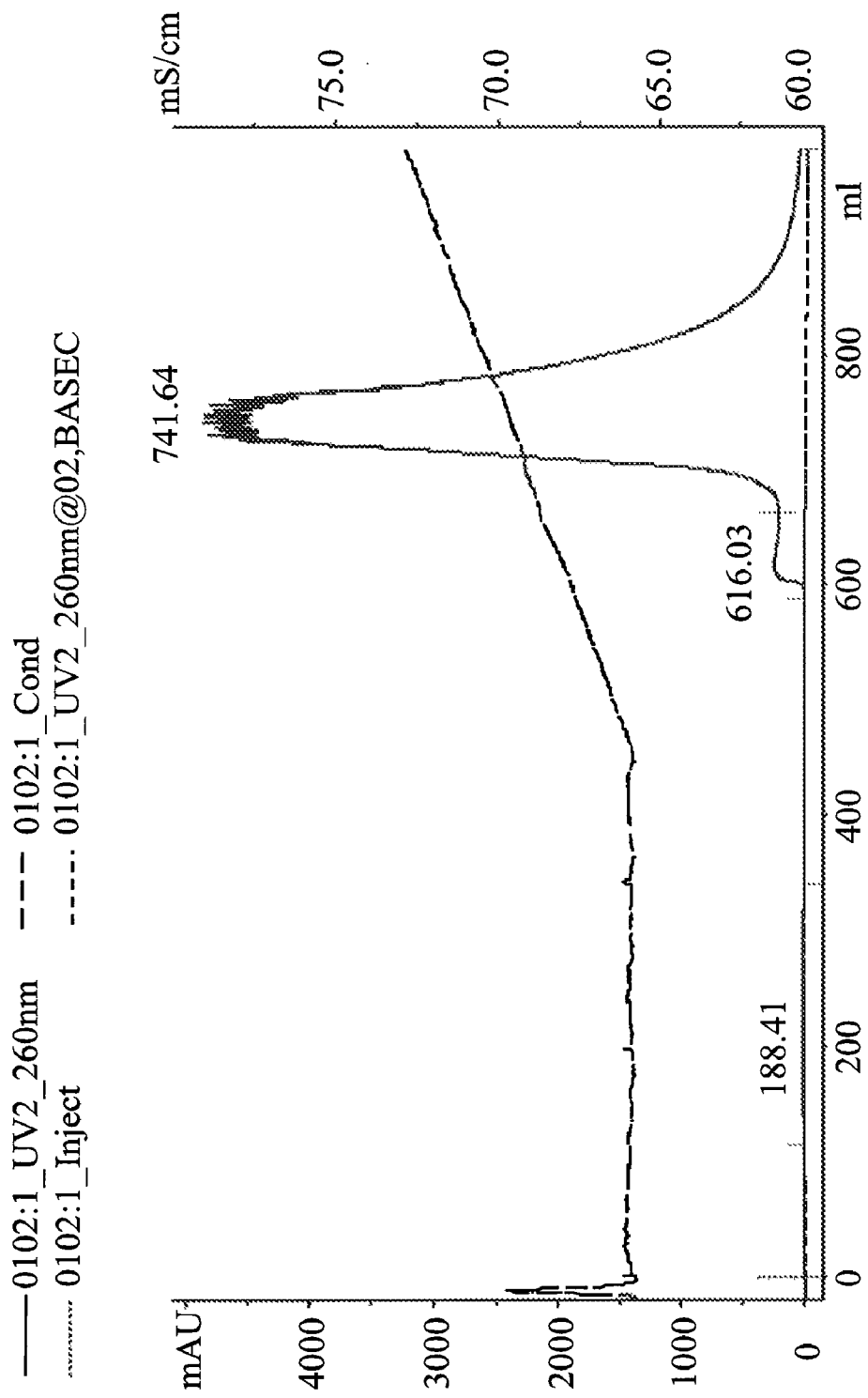
FIG. 20 shows a chromatographic profile and analysis of plasmid DNA following fine RNA removal and concentration, with SDS.

FIG. 20 shows the chromatographic profile and analysis data of plasmid DNA after Fine RNA removal (Step 8) using diafiltration at +50° C. temperature. NA concentration/diafiltration (Step 6) with 0.1% SDS . Semi preparative anion exchange chromatography on Q Sepharose HP XK-26 column; column volume—125 cm$^3$, Buffer A—10 mM Tris, pH 8.0, 1 mM EDTA, 0.70M NaCl, λ=66 mS/cm, Buffer B—10 mM Tris, pH 8.0, 1 mM EDTA, 0.90 M NaCl, λ=84 mS/cm, gradient flow rate—45 cm/h. Analysis of the chromatogram is as follows:

| No | Peak name | Ret (ml) | Area (mAU * ml) | Area/Peak area ((volume)%) | Height (mAU) |
|---|---|---|---|---|---|
| 1 | Relaxed form of plasmid DNA | 616.03 | 13638.3239 | 3.15 | 246.610 |
| 3 | Supercoiled form of plasmid DNA | 741.64 | 416982.8787 | 96.20 | 861.060 |

Total area (mAU * ml) 43394.2683
Area in evaluated peaks (mAU * ml) 433471.1200
Ratio peak area/total area 0.998900
Total peak width (ml) 615.68

-continued

| No | Peak name | Ret (ml) | Area (mAU * ml) | Area/Peak area ((volume)%) | Height (mAU) |
|----|-----------|----------|-----------------|----------------------------|--------------|

Calculated from Q Sepharose HP 0102:1_UV2_260 nm
Baseline Q Sepharose HP 0102:1_UV2_260 nm@02, BASEC
Current peak filter settings
Maximum number of peaks ( ) 20

Figure 21:
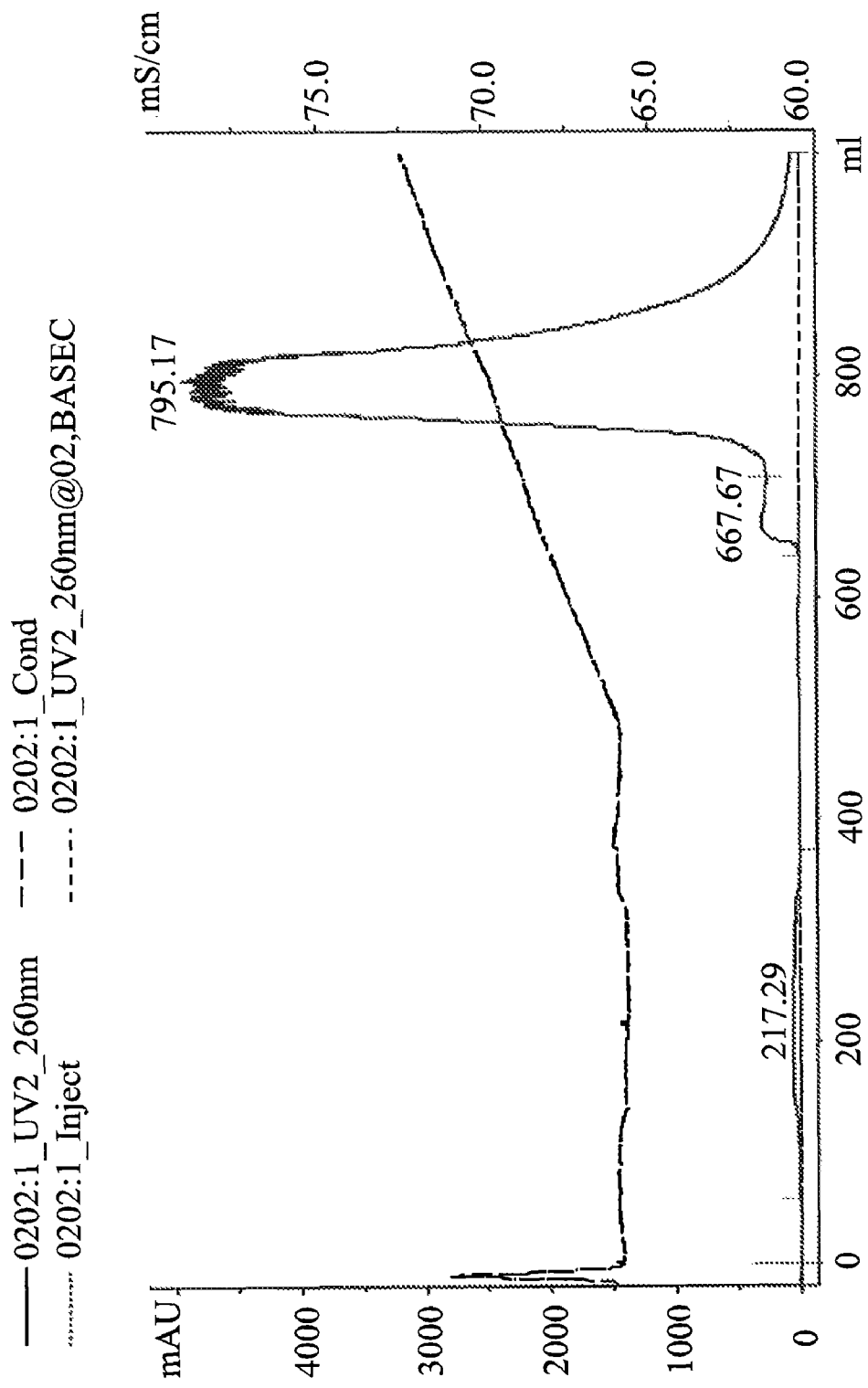
FIG. 21 shows a chromatographic profile and analysis of plasmid DNA following fine RNA removal and concentration, without SDS.

FIG. 21 shows the chromatographic profile and analysis data of plasmid DNA after Fine RNA removal (Step 8) using diafiltration at +50° C. temperature. NA concentration/diafiltration (Step 6) without 0.1%. Semi preparative anion exchange chromatography on Q Sepharose HP XK-26 column; column volume—125 cm$^3$, Buffer A—10 mM Tris, pH 8.0, 1 mM EDTA, 0.70M NaCl, λ=66 mS/cm, Buffer B—10 mM Tris, pH 8.0, 1 mM EDTA, 0.90 M NaCl, λ=84 mS/cm, gradient flow rate—45 cm/h. Analysis of the chromatogram is as follows:

| No | Peak name | Ret (ml) | Area (mAU * ml) | Area/Peak area ((volume)%) | Height (mAU) |
|----|-----------|----------|-----------------|----------------------------|--------------|
| 1 | RNA | 217.29 | 10709.5104 | 2.29 | 58.920 |
| 2 | Relaxed form of plasmid DNA | 667.67 | 15872.7195 | 3.39 | 297.470 |
| 3 | Supercoiled form of plasmid DNA | 795.17 | 441913.3352 | 94.33 | 4953.590 |

Total area (mAU * ml) 468832.3410
Area in evaluated peaks (mAU * ml) 468495.5651
Ratio peak area/total area 0.999282
Total peak width (ml) 679.16
Calculated from Q Sepharose HP 0202:1_UV2_260 nm
Baseline Q Sepharose HP 0202:1_UV2_260 nm@02, BASEC
Current peak filter settings
Maximum number of peaks ( ) 20

Step 11. Pooled plasmid DNA diafiltration and DNA concentration: The pooled plasmid DNA solutions from both plasmid preparations were diafiltered in parallel using one 100 kDa NMWL screen channel ultrafiltration Minisette Systems Cassettes with Omega Membrane (PALL FILTRON, USA), installed in Minisette Lab Tangential Flow System (PALL FILTRON, USA) ultrafiltration device. 0.22 m filtrated TE buffer was used for diafiltration of the plasmid DNA solutions. The initial volume of DNA solutions was six times reduced by ultrafiltration and loading buffer was added to restore the initial volume. Three cycles of diafiltration were performed. Plasmid DNA diafiltrate volume in the last diafiltration cycle was reduced to obtain DNA concentration in the range of 4-5 mg/ml. Diafiltrate was decanted and the ultrafiltration system was flushed with TE buffer volume to collect the residual plasmid DNA and dilute DNA up to 1.8-2.2 mg/ml concentration.

Step 12. Bulk plasmid DNA preparation: The plasmid DNA solution at a final concentration was prepared and submitted to the sterile filtration into apyrogenic containers. Samples for quality control were taken. Containers were labelled with a description of the product lot #, volume, concentration, date of production and were stored frozen.

Yields of test plasmid DNA after purification processes described above are presented in Table 1 for ultrafiltration with 0.1% SDS and in Table 2 for ultrafiltration without 0.1% SDS.

Amount of polysaccharides, including lipopolysaccharides, synthesized in E.coli cells depends greatly from the cultivation conditions, such as carbon/nitrogen ratio in the cultural medium, inoculate life, etc. Amount of synthesized polysaccharides is also greatly dependent on particular E.coli strain that is chosen as plasmid DNA producent. As a rule, if in the beginning of E.coli fermentation 2-3 hours lag phase is observed, biomass obtained in such fermentation is characterised by increased amounts of polysaccharides that significantly complicate further plasmid DNA purification and decrease qualitative parameters of the final product. To minimise negative polysaccharide influence on the plasmid purification process and quality, we have modified composition of TE buffer used in Step 5: Nucleic acid (NA) concentration and diafiltration and have introduced additional hydrophobic chromatography step into purification scheme. Maintenance of 0.1% SDS concentration during diafiltration allowed for more efficient elimination of cellular polysaccharides and other contaminants of product origin compared to the standard TE buffer (10 mM Tris-HCl, pH 8.0, 1 mM EDTA) used in the previous experiment. Hydrophobic chromatography is used as an additional step that ensures that endotoxin and cellular protein contamination level in the final plasmid DNA preparation conforms to the requirements set for pharmaceutical compounds.

Example No 2 illustrates purification process of pUC type plasmid DNA from E.coli JM109 strain product biomass. During the fermentation of this biomass almost 3 hours lag phase was registered, that resulted in the increased amount of polysaccharides and endotoxins. Summarised results of the purification process performed in Example No 2 are presented in Table 3 and Table 4. Diafiltration in Step 5 against TE buffer supplemented with 0.1% SDS allowed the preparation of plasmid DNA solution (concentrate after Step 8. Fine RNA removing), that was characterised by thousand times lower lipopolysaccharides content compared to that obtainable when using standard TE buffer: 6800 EU/ml instead of 7000000 EU/ml respectively. Use of 0.1% SDS also improved the elimination of remaining low molecular mass RNA in Step 8: Fine RNA Removing: 0.8% RNA, when using TE buffer with 0, 1% SDS instead of 2, 3%, when standard TE buffer was used. Removal of E.coli cell proteins was much more efficient when using 0.1% SDS: 45 ng/ml instead of 126 ng/ml. Hydrophobic chromatography was more efficient when used in combination with ultrafiltration in the presence of 0.1% SDS and enabled a further reduction of cellular contaminants level of at least ten times, that after anion exchange chromatography step, in turn, resulted in plasmid DNA with highest quality parameters set at present for therapic plasmid DNA.

It is evident from presented data that temperature elevation from room temperature (20° C.) to 40° C. during the concentration of NA solution (Step 5) allowed to increase the ultrafiltration speed (average filtrate flow speed) about two times, i.e. from 58 to 120 ml/min in described experiment, while maintaining the same parameters of ultrafiltration process, namely, the NA solution supply speed (1100 ml/min) and the pressure in the ultrafiltration unit (20 psi), and subsequently reduced the duration of concentration step at least twice.

Diafiltration and concentration of NA solution in TE buffer in step 5 when followed by subsequent $CaCl_2$ treatment in step allows the elimination of the majority of E.coli RNA, genomic DNA, cell proteins and large amounts lipopolysaccharides. DNA electrophoretic analysis (lanes 3 and 5 in FIG. 20) and SDS PAGE analysis (lanes 2 and 4 in FIG. 21) as well as plasmid DNA chromatographic analysis (FIGS. 14 and 15) indicate that concentration and diafiltration of NA solution increased the efficiency of the subsequent $CaCl_2$ treatment and effectively reduced the amount of contaminants. According to our data CaCl$_2$ treatment performed immediately after the acetate neutralisation step (Step 3, 4) is not that efficient and significantly higher amounts of contaminants of *E.coli* origin, such as different RNAs and their degradation products, are retained in the solution.

RNA diafiltration at 50° C. temperature and high (0, 70 M) NaCl concentration in step 8 allowed to reduce the amount of RNR/polysaccharide/protein contaminants to 1, 51% according to absorption at 260 nm, while the same step performed at the room temperature reduced the total amount of contaminating substances to 3, 01% according to semi preparative anion exchange chromatography data (FIG. 18, 19). Having in mind that usually polysaccharides constitute about 30% of RNA/polysaccharides peak (data from FIG. 16, 17) the final RNA amount in the plasmid DNA solution after Fine RNA removal step at 50° C. temperature constituted only about 1% from the total absorption at 260 nm. Fine RNA removal step carried out at room temperature was quite efficient as well, however, the final RNA amount constituted 2%. According to SDS-PAGE (FIG. 21) analysis results, the cell proteins remaining after the Initial precipitation of RNA with CaCl$_2$ step are effectively eliminated during diafiltration at step 8 (lanes 4 and 10). Moreover, experimental data indicate that diafiltration at 50° C. results in the lower amount of contaminating proteins than the same procedure performed at the room temperature (FIG. 21, lane 10). Anion exchange chromatography step 9 constitutes the final step of plasmid DNA purification process after which obtained plasmid DNA conforms in its characteristics to the requirements for therapeutic grade DNA (endotoxin concentration is already lower than 0, 10EU/μg DNA, Tables 3 and 4). Diafiltration step used afterwards allows to obtain the final preparation of purified plasmid DNA dissolved in the solution having desired composition.

TABLE 3

Results of plasmid DNA purification using nucleic acid concentration and diafiltration method with 0.1% SDS

| Purification Stage | Volume, ml | Endotoxin content, EU/ml | Amount of host cell protein, ng/ml | Total amount of nucleic acid, mg | RNA/DNA content | | DNA yield, % |
|---|---|---|---|---|---|---|---|
| | | | | | RNA amount, mg | DNA amount, mg | |
| Cell debris removal, supernatant | 2440 | | | | | | |
| Nucleic acid (NA) concentration and diafiltration, concentrate of NA | 360 | | | | — | — | |
| Initial precipitation of RNA with CaCl$_2$, supernatant | 435 | | | 268 | 142 | 126 | 100 |
| Fine RNA removal | | | | | | | |
| Concentrate | 205 | 6800 | 45 | 123 | 1 | 122 | 97 |
| Diafiltrate | 4000 | | | 132 | 132 | | |
| Hydrophobic chromatography | 203 | 400 | 3 | 117 | 1 | 116 | 92 |
| Anion exchange chromatography, pool of appropriate fractions | 120 | 3 | 0.3 | 104 | | 104 | 83 |

TABLE 4

Results of plasmid DNA purification using nucleic acid concentration and diafiltration method without 0.1% SDS

| Purification Stage | Volume, ml | Endotoxin content, EU/ml | Amount of *E. coli* host protein, ng/ml | Total amount of nucleic acid, mg | RNA/DNA content | | DNA yield, % |
|---|---|---|---|---|---|---|---|
| | | | | | RNA amount, mg | DNA amount, mg | |
| Cell debris removal, supernatant | 2440 | | | | | | |
| Nucleic acid (NA) concentration and diafiltration, concentrate of NA | 360 | | | | — | — | |
| Initial precipitation of RNA with CaCl$_2$, supernatant | 425 | | | 295 | 164 | 131 | 100 |
| Fine RNA removal | | | | | | | |
| Concentrate | 205 | $7.0 \times 10^6$ | 126 | 128 | 3 | 125 | 95 |
| Diafiltrate | 4000 | | | 142 | 142 | | |

TABLE 4-continued

Results of plasmid DNA purification using nucleic acid concentration and diafiltration method without 0.1% SDS

| Purification Stage | Volume, ml | Endotoxin content, EU/ml | Amount of E. coli host protein, ng/ml | Total amount of nucleic acid, mg | RNA amount, mg | DNA amount, mg | DNA yield, % |
|---|---|---|---|---|---|---|---|
| Hydrophobic chromatography | 203 | >360000 | 112 | 125 | 2 | 123 | 94 |
| Anion exchange chromatography, pool of appropriate fractions | 120 | 2200 | 28 | 110 | | 110 | 84 |

The invention claimed is:

1. A process for purifying plasmid DNA from a nucleic acid-containing sample comprising plasmid DNA and contaminants including RNA, which process comprises a step of contaminant removal, comprising:
   (a) treating the nucleic acid-containing sample to form a nucleic acid solution having a concentration of monovalent cations selected from the group consisting of sodium and potassium, which nucleic acid solution includes the RNA;
   (b) contacting the nucleic acid solution comprising the plasmid DNA and RNA with an ultrafiltration membrane having a molecular weight exclusion limit of at least 30 kDa and no more than 100 kDa, which ultrafiltration membrane is provided in a screen-channel ultrafiltration unit which generates turbulent sample flow, whereby turbulence is provided in the region of the ultrafiltration membrane, wherein the step of contacting includes a step of diafiltration and wherein the step of contacting and the step of diafiltering the nucleic acid solution with the ultrafiltration membrane takes place in the presence of a concentration of the monovalent cations which is at least about 0.35M but does not exceed about 2M for a time sufficient to remove substantially all RNA and form a retentate containing plasmid DNA; and
   (c) collecting the retentate.

2. A process according to claim 1, wherein the molecular weight exclusion limit of the ultrafiltration membrane is at least 50 kDa and no more than 100 kDa.

3. A process according to claim 1, wherein at least step (b) is performed at a temperature in the range 30° C. to 60° C.

4. A process according to claim 1, which further comprises a step (d) of subjecting the retentate to further purification.

5. A process according to claim 4, wherein step (d) comprises: (i) contacting the retentate with an anion exchange resin under conditions to bind plasmid DNA; (ii) optionally washing the resin to remove impurities from the plasmid DNA; and (iii) eluting the plasmid DNA.

6. A process according to claim 4, wherein the retentate is contacted with a hydrophobic solid phase under conditions to separate contaminants from plasmid DNA.

7. A process according to claim 1, wherein the nucleic acid-containing sample is prepared from a crude nucleic acid solution containing plasmid DNA and RNA by (i) treating the crude nucleic acid solution to provide a calcium ion concentration sufficient to precipitate a majority of the RNA; and (ii) separating the liquid phase therefrom, the liquid phase comprising the nucleic acid-containing sample.

8. A process according to claim 7, wherein the calcium ion concentration is in the range 0.1 to 0.3M.

9. A process according to claim 7, wherein the crude nucleic acid solution is prepared by (i) providing a cell free extract comprising plasmid DNA and RNA; and (ii) concentrating the extract by ultrafiltration.

10. A process according to claim 9, wherein at least step (ii) is performed at a temperature in the range 30° C. to 60° C.

11. A process according to claim 9, which further comprises a step of diafiltration against a solution suitable for use in the subsequent step of treating the solution to provide a calcium ion concentration sufficient to precipitate the majority of RNA.

12. A process according to claim 9, wherein the ultrafiltration is carried out in the presence of a detergent.

13. A process according to claim 12, wherein the detergent comprises sodium dodecylsulphate.

14. A process for plasmid DNA purification from a nucleic acid containing sample comprising plasmid DNA and contaminants including RNA, which process comprises a step of contaminant removal, comprising:
   (a) treating the nucleic acid containing sample to form a nucleic acid solution having a concentration of monovalent cations selected from the group consisting of sodium and potassium, which nucleic acid solution includes the RNA;
   (b) contacting the nucleic acid solution comprising the plasmid DNA and RNA with an ultrafiltration membrane having a molecular weight exclusion limit of at least 30 kDa and no more than 100 kDa, which ultrafiltration membrane is provided in a screen-channel ultrafiltration unit which generates turbulent sample flow, whereby turbulence is provided in the region of the ultrafiltration membrane, wherein the step of contacting includes a step of diafiltration and wherein the step of contacting and the step of diafiltering the nucleic acid solution with the ultrafiltration membrane takes place in the presence of a concentration of the monovalent cations which is at least about 0.35M but does not exceed about 2M for a time sufficient to remove all RNA and form a retentate containing plasmid DNA;
   (c) collecting the retentate;
   (d) subjecting the retentate to hydrophobic chromatography;
   (e) contacting the retentate with an anion exchange resin under conditions to bind plasmid DNA;
   (f) optionally washing the resin to remove impurities from the plasmid DNA; and
   (g) eluting the plasmid DNA.

15. A process for purifying plasmid DNA from a nucleic acid-containing sample comprising plasmid DNA and contaminants including RNA, which process comprises a step of contaminant removal, comprising:
(a) treating the nucleic acid-containing sample to form a nucleic acid solution having a concentration of monovalent cations selected from the group consisting of sodium and potassium, which nucleic acid solution includes the RNA;
(b) contacting the nucleic acid solution comprising the plasmid DNA and RNA with an ultrafiltration membrane having a molecular weight exclusion limit of at least 30 kDa and no more than 100 kDa, which ultrafiltration membrane is provided in a screen-channel ultrafiltration unit which generates turbulent sample flow, whereby turbulence is provided in the region of the ultrafiltration membrane, wherein the step of contacting includes a step of diafiltration and wherein the step of contacting and the step of diafiltering the nucleic acid solution with the ultrafiltration membrane takes place in the presence of a concentration of the monovalent cations which is at least about 0.35M but does not exceed about 2M for a time sufficient to remove substantially all RNA and form a retentate containing plasmid DNA; and
(c) collecting the retentate,
wherein the nucleic acid solution is contacted with the ultrafiltration membrane under pressure and at a temperature range of room temperature to 60° C.

16. A process for purifying plasmid DNA from a nucleic acid-containing sample comprising plasmid DNA and contaminants including RNA, which process comprises a step of contaminant removal, comprising:
(a) treating the nucleic acid-containing sample to form a nucleic acid solution having a concentration of monovalent cations selected from the group consisting of sodium and potassium, which nucleic acid solution includes the RNA;
(b) contacting the nucleic acid solution comprising the plasmid DNA and RNA with an ultrafiltration membrane having a molecular weight exclusion limit of at least 30 kDa and no more than 100 kDa, which ultrafiltration membrane is provided in a screen-channel ultrafiltration unit which generates turbulent sample flow, whereby turbulence is provided in the region of the ultrafiltration membrane, wherein the step of contacting includes a step of diafiltration and wherein the step of contacting and the step of diafiltering the nucleic acid solution with the ultrafiltration membrane takes place in the presence of a concentration of the monovalent cations which is at least about 0.35M but does not exceed about 2M for a time sufficient to remove substantially all RNA and form a retentate containing plasmid DNA; and
(c) collecting the retentate,
wherein the nucleic acid solution is contacted with the ultrafiltration membrane under a pressure range of 15 to 30 psi and at a temperature range of room temperature to 60° C.

17. A process for purifying plasmid DNA from a nucleic acid-containing sample comprising plasmid DNA and contaminants including RNA, which process comprises a step of contaminant removal, comprising:
(a) treating the nucleic acid-containing sample to form a nucleic acid solution having a concentration of monovalent cations selected from the group consisting of sodium and potassium, which nucleic acid solution includes the RNA;
(b) contacting the nucleic acid solution comprising the plasmid DNA and RNA with an ultrafiltration membrane having a molecular weight exclusion limit of at least 30 kDa and no more than 100 kDa, which ultrafiltration membrane is provided in a screen-channel ultrafiltration unit which generates turbulent sample flow, whereby turbulence is provided in the region of the ultrafiltration membrane, wherein the step of contacting includes a step of diafiltration and wherein the step of contacting and the step of diafiltering the nucleic acid solution with the ultrafiltration membrane takes place in the presence of a concentration of the monovalent cations which is at least about 0.35M but does not exceed about 2M for a time sufficient to remove RNA and form a retentate containing plasmid DNA; and
(c) collecting the retentate,
wherein the nucleic acid solution is contacted with the ultrafiltration membrane under a pressure range of 15 to 30 psi and a temperature range of room temperature to 60° C.

18. A process for purifying plasmid DNA from a nucleic acid-containing sample comprising plasmid DNA and contaminants including RNA, which process comprises a step of contaminant removal, comprising:
(a) treating the nucleic acid-containing sample to form a nucleic acid solution having a concentration of monovalent cations selected from the group consisting of sodium and potassium, which nucleic acid solution includes the RNA;
(b) contacting the nucleic acid solution comprising the plasmid DNA and RNA with an ultrafiltration membrane having a molecular weight exclusion limit of at least 30 kDa and no more than 100 kDa, which ultrafiltration membrane is provided in a screen-channel ultrafiltration unit including a separator positioned between a pair of membranes which generates turbulent sample flow, whereby turbulence is provided in the region of the ultrafiltration membrane, wherein the step of contacting includes a step of diafiltration and wherein the step of contacting and the step of diafiltering the nucleic acid solution with the ultrafiltration membrane takes place in the presence of a concentration of the monovalent cations which is at least about 0.35M but does not exceed about 2M for a time sufficient to remove RNA and form a retentate containing plasmid DNA; and
(c) collecting the retentate,
wherein the nucleic acid solution is contacted with the ultrafiltration membrane under a pressure range of 15 to 30 psi and a temperature range of room temperature to 60° C.

* * * * *